(12) United States Patent
Zdeblick et al.

(10) Patent No.: US 7,200,439 B2
(45) Date of Patent: Apr. 3, 2007

(54) METHOD AND APPARATUS FOR ENHANCING CARDIAC PACING

(75) Inventors: Mark Zdeblick, Portola Valley, CA (US); Joseph M. Ruggio, Laguna Hills, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 379 days.

(21) Appl. No.: 10/764,429

(22) Filed: Jan. 23, 2004

(65) Prior Publication Data

US 2004/0220637 A1 Nov. 4, 2004

Related U.S. Application Data

(60) Provisional application No. 60/451,176, filed on Feb. 27, 2003, provisional application No. 60/458,656, filed on Mar. 27, 2003, provisional application No. 60/442,376, filed on Jan. 24, 2003, provisional application No. 60/442,441, filed on Jan. 24, 2003.

(51) Int. Cl.
*A61N 1/365* (2006.01)
(52) U.S. Cl. ............................. 607/17; 607/27; 607/28
(58) Field of Classification Search .................. 607/4, 607/9, 17–28; 600/523
See application file for complete search history.

(56) References Cited

U.S. PATENT DOCUMENTS

| | | | |
|---|---|---|---|
| 4,397,314 A | 8/1983 | Vaguine |
| 4,399,820 A | 8/1983 | Wirtzfeld et al. |
| 4,603,705 A | 8/1986 | Speicher et al. |
| 4,628,934 A | 12/1986 | Pohndorf et al. |
| 4,776,334 A | 10/1988 | Prionas |
| 4,815,472 A | 3/1989 | Wise et al. |
| 4,877,032 A | 10/1989 | Heinze et al. |

(Continued)

FOREIGN PATENT DOCUMENTS

EP 1 266 606 12/2002

(Continued)

OTHER PUBLICATIONS

Receveur et al., "Latterally Moving Bi-Stable MEMS DC-Switch for Biomedical Applications," Medtronic Bakken Research Center, The Netherlands (2004), pp. 854-856.

(Continued)

*Primary Examiner*—Robert Pezzuto
*Assistant Examiner*—Yun Haeng Lee
(74) *Attorney, Agent, or Firm*—Bret E. Field; Bozicevic, Field & Francis LLP; Kathleen McCowin

(57) ABSTRACT

Methods, apparatus and systems for enhancing cardiac pacing generally provide for measuring at least one cardiac characteristic, calculating at least one cardiac performance parameter based on the measured characteristic(s), and adjusting at least one functional parameter of a cardiac pacing device. Devices may include at least one catheter (such as a multiplexed catheter with one or more sensors and/or actuators), at least one implant (such as a sensor implantable in a heart wall), or a combination of both. Various cardiac performance parameters and/or pacing device performance parameters may be weighted, and the parameters and their respective weights may be used to determine one or more adjustments to be made to the pacing device. In some instances, the adjustments are made automatically.

99 Claims, 7 Drawing Sheets

U.S. PATENT DOCUMENTS

| | | | |
|---|---|---|---|
| 4,878,898 A | 11/1989 | Griffin et al. | |
| 4,881,410 A | 11/1989 | Wise et al. | |
| 4,902,273 A | 2/1990 | Choy et al. | |
| 5,004,275 A | 4/1991 | Miller | |
| 5,035,246 A | 7/1991 | Heuvelmans et al. | |
| 5,072,737 A | 12/1991 | Goulding | |
| 5,113,868 A | 5/1992 | Wise et al. | |
| 5,156,154 A | 10/1992 | Valenta, Jr. et al. | |
| 5,188,106 A * | 2/1993 | Nappholz et al. | 607/24 |
| 5,213,098 A | 5/1993 | Bennett et al. | |
| 5,305,745 A | 4/1994 | Zacouto et al. | |
| 5,391,199 A | 2/1995 | Ben-Haim | |
| 5,411,532 A | 5/1995 | Mortazavi | |
| 5,411,537 A | 5/1995 | Munshi et al. | |
| 5,417,717 A | 5/1995 | Salo et al. | |
| 5,419,767 A | 5/1995 | Eggers et al. | |
| 5,423,323 A | 6/1995 | Orth | |
| 5,509,411 A | 4/1996 | Littmann et al. | |
| 5,535,752 A | 7/1996 | Halperin et al. | |
| 5,544,656 A | 8/1996 | Pitsillides et al. | |
| 5,549,650 A | 8/1996 | Bornzin et al. | |
| 5,579,764 A | 12/1996 | Goldreyer | |
| 5,591,142 A | 1/1997 | Van Erp | |
| 5,593,430 A | 1/1997 | Renger | |
| 5,662,587 A | 9/1997 | Grundfest et al. | |
| 5,683,429 A | 11/1997 | Mehra | |
| 5,720,768 A | 2/1998 | Verboven-Nelissen | |
| 5,743,267 A | 4/1998 | Nikolic et al. | |
| 5,788,647 A | 8/1998 | Eggers | |
| 5,800,465 A | 9/1998 | Thompson et al. | |
| 5,810,735 A | 9/1998 | Halperin et al. | |
| 5,814,089 A | 9/1998 | Stokes et al. | |
| 5,902,234 A | 5/1999 | Webb | |
| 5,902,248 A | 5/1999 | Millar et al. | |
| 5,913,814 A | 6/1999 | Zantos | |
| 5,924,997 A | 7/1999 | Campbell | |
| 5,935,084 A | 8/1999 | Southworth | |
| 5,999,848 A | 12/1999 | Gord et al. | |
| 6,015,386 A | 1/2000 | Kensey et al. | |
| 6,024,704 A | 2/2000 | Meador et al. | |
| 6,033,398 A | 3/2000 | Farley et al. | |
| 6,038,480 A | 3/2000 | Hrdlicka et al. | |
| 6,078,830 A | 6/2000 | Levin et al. | |
| 6,081,748 A | 6/2000 | Struble et al. | |
| 6,155,267 A | 12/2000 | Nelson | |
| 6,165,135 A | 12/2000 | Neff | |
| 6,171,252 B1 | 1/2001 | Roberts | |
| 6,206,835 B1 | 3/2001 | Spillman, Jr. et al. | |
| 6,206,874 B1 | 3/2001 | Ubby et al. | |
| 6,234,973 B1 | 5/2001 | Meador et al. | |
| 6,264,606 B1 | 7/2001 | Ekwall et al. | |
| 6,277,078 B1 | 8/2001 | Porat et al. | |
| 6,287,256 B1 | 9/2001 | Park et al. | |
| 6,299,582 B1 | 10/2001 | Brockway et al. | |
| 6,301,500 B1 | 10/2001 | Van Herk et al. | |
| 6,309,350 B1 | 10/2001 | Van Tassel et al. | |
| 6,309,385 B1 | 10/2001 | Simpson | |
| 6,328,699 B1 | 12/2001 | Eigler et al. | |
| 6,360,123 B1 | 3/2002 | Kimchi et al. | |
| 6,363,279 B1 | 3/2002 | Ben-Haim et al. | |
| 6,370,431 B1 | 4/2002 | Stoop et al. | |
| 6,418,348 B1 | 7/2002 | Witte | |
| 6,438,408 B1 | 8/2002 | Mulligan et al. | |
| 6,466,820 B1 | 10/2002 | Juran et al. | |
| 6,473,653 B1 | 10/2002 | Schallhorn et al. | |
| 6,477,395 B2 | 11/2002 | Schuman et al. | |
| 6,477,417 B1 | 11/2002 | Levine | |
| 6,496,730 B1 | 12/2002 | Kleckner et al. | |
| 6,580,946 B2 | 6/2003 | Struble | |
| 6,611,714 B1 | 8/2003 | Mo | |
| 6,628,989 B1 | 9/2003 | Penner et al. | |
| 6,666,826 B2 | 12/2003 | Salo et al. | |
| 2001/0047138 A1 | 11/2001 | Kokate et al. | |
| 2001/0053882 A1 | 12/2001 | Haddock et al. | |
| 2002/0026183 A1 | 2/2002 | Simpson | |
| 2002/0045921 A1 | 4/2002 | Wolinsky et al. | |
| 2002/0077568 A1 | 6/2002 | Haddock | |
| 2002/0077673 A1 | 6/2002 | Penner et al. | |
| 2002/0095196 A1 | 7/2002 | Linberg | |
| 2002/0111560 A1 | 8/2002 | Kokate et al. | |
| 2002/0120186 A1 | 8/2002 | Keimel | |
| 2002/0151816 A1 | 10/2002 | Rich et al. | |
| 2002/0156417 A1 | 10/2002 | Rich et al. | |
| 2002/0161307 A1 | 10/2002 | Yu et al. | |
| 2002/0169445 A1 | 11/2002 | Jain et al. | |
| 2003/0153952 A1 | 8/2003 | Auricchio et al. | |
| 2004/0193021 A1 | 9/2004 | Zdeblick et al. | |
| 2004/0215049 A1 | 10/2004 | Zdeblick et al. | |
| 2004/0254483 A1 | 12/2004 | Zdeblick et al. | |

FOREIGN PATENT DOCUMENTS

| | | |
|---|---|---|
| FR | 2 097 337 | 3/1972 |
| WO | WO 02/065894 A2 | 8/2002 |
| WO | WO 2004/052182 A2 | 6/2004 |
| WO | WO 2004/052182 A3 | 6/2004 |
| WO | WO 2004/066814 A2 | 8/2004 |
| WO | WO 2004/066814 A3 | 8/2004 |
| WO | WO 2004/066817 A2 | 8/2004 |
| WO | WO 2004/066817 A3 | 8/2004 |
| WO | WO 2004/067081 A2 | 8/2004 |
| WO | WO 2004/067081 A3 | 8/2004 |

OTHER PUBLICATIONS

Auricchio et al., "The Pacing Therapies for Congestive Heart Failure (PATH-CHF) Study: Rationale, Design, and Endpoints of a Prospective Randomized Multicenter Study," Am J Cardiol, 1999; 83:130D-135D.

Borky, J.M. and Wise, K.D., "Integrated Signal Conditioning for Silicon Pressure Sensors" *IEEE Transactions on Electron Devices*, vol. ED-26, No. 12 (Dec. 1979) pp. 1906-1910.

Kovacs, "Technology Development For A Chronic Neutral Interface", A dissertation, Stanford University (Aug. 1990), pp. 9, 225-234, 257, 276.

* cited by examiner

FIG_1

FIG_2

FIG — 3

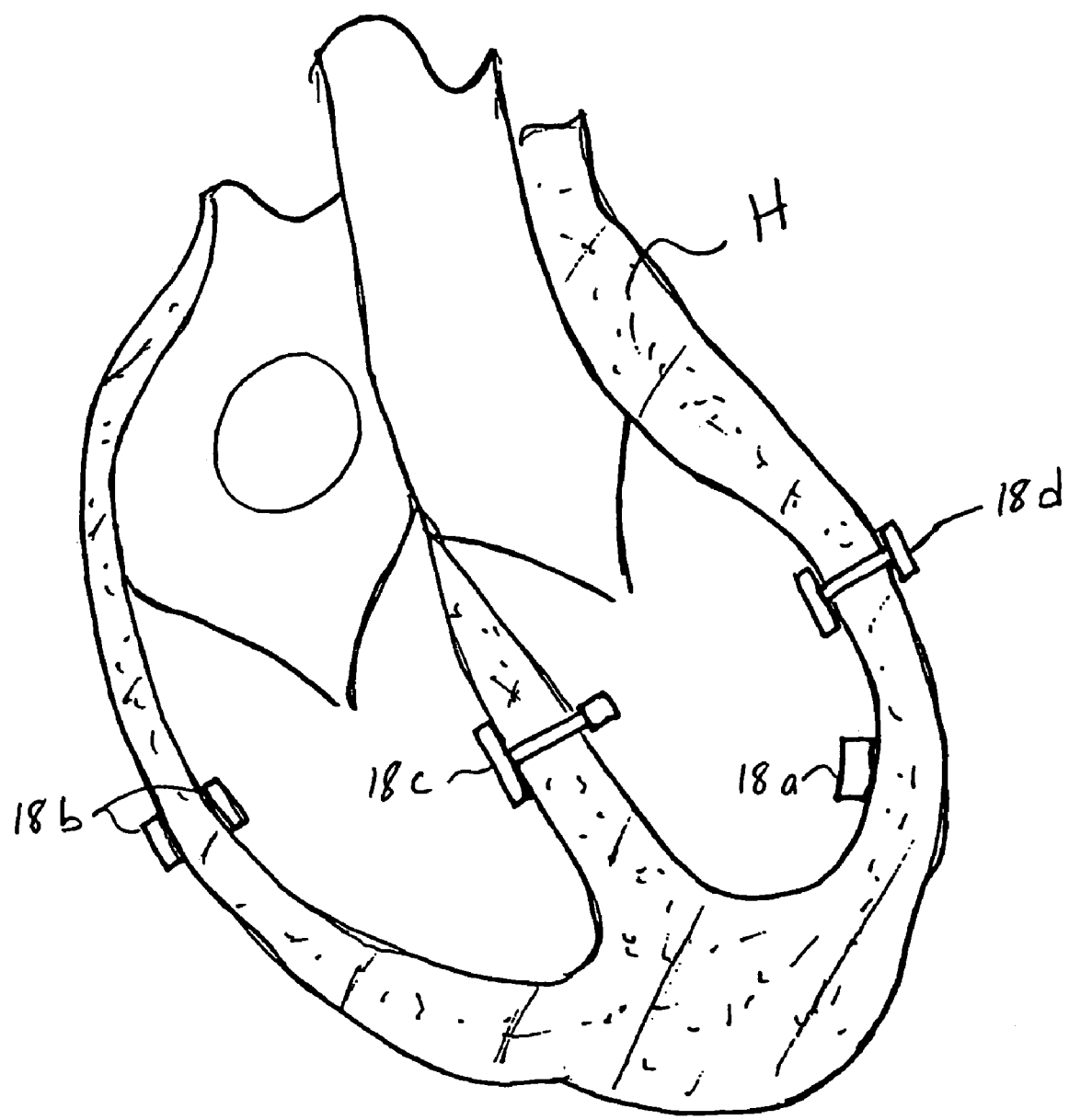
FIG—5

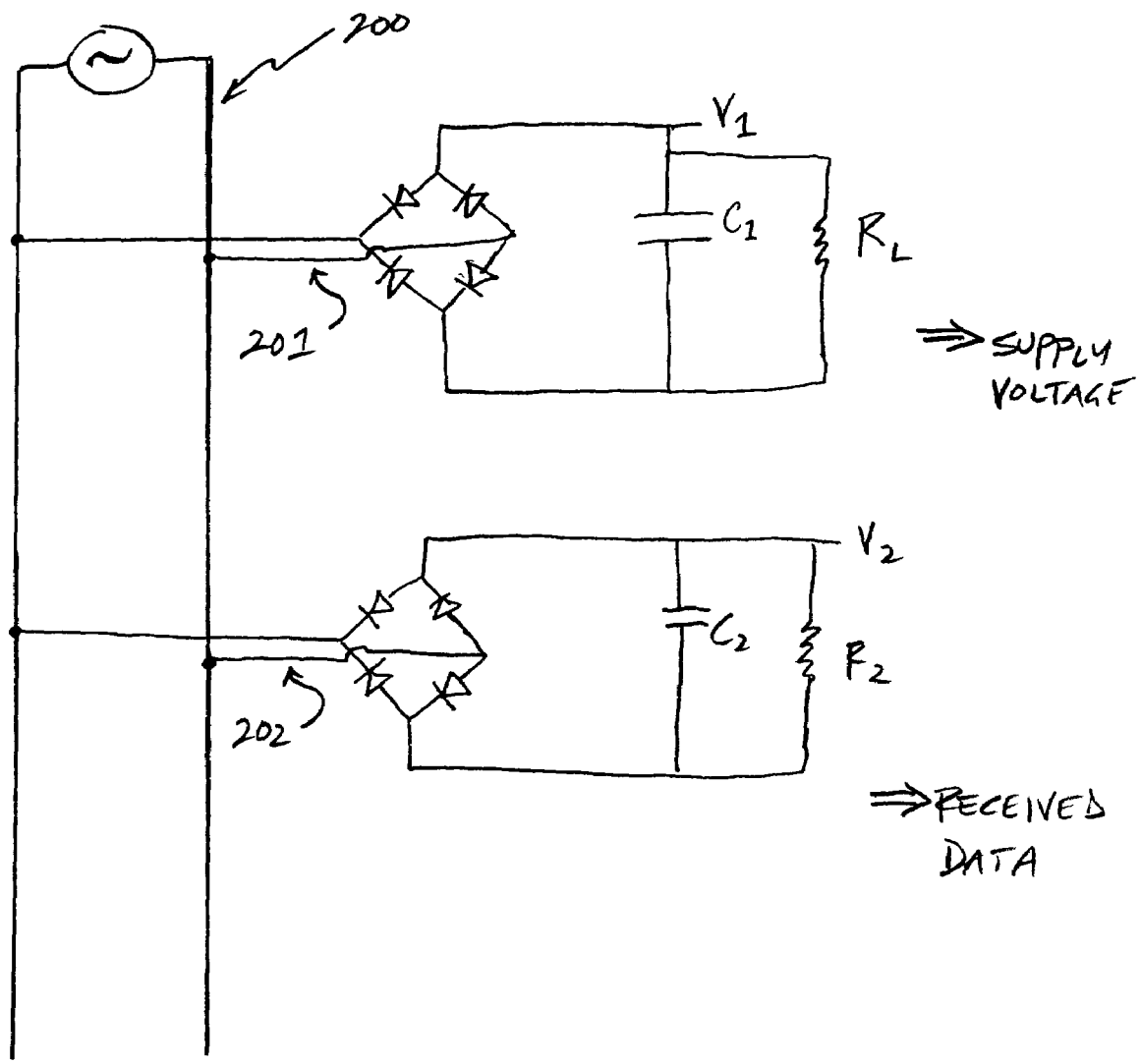
FIG_5A

METHOD AND APPARATUS FOR ENHANCING CARDIAC PACING

CROSS REFERENCE TO RELATED APPLICATIONS

The present application claims the priority benefit of U.S. Provisional Patent Application Nos.: 60/442,376, filed Jan. 24, 2003; 60/442,441, filed Jan. 24, 2003; 60/451,176, filed Feb. 27, 2003; and 60/458,656, filed Mar. 27, 2003. The disclosures of all of these Provisional Patent Applications are hereby incorporated fully by reference.

BACKGROUND OF THE INVENTION

The present invention relates generally to medical methods, apparatus and systems. More specifically, the invention relates to methods, apparatus and systems for enhancing cardiac pacing.

Defects in the electrical conduction system of the heart can lead to a number of potentially life-threatening conditions, such as congestive heart failure (CHF), a fatal cardiac arrhythmia or the like. Implantable devices used to provide electrical pacing of a heart to treat defects in the heart's conduction system, typically called cardiac pacemakers, are known. Such implantable devices work in a variety of ways and may provide electric pulses to multiple areas of a heart. Biventricular pacing devices, for example, provide pulses to both the left and right ventricles of the heart using multiple leads.

In many instances, it may be advantageous to provide cardiac pacing to a heart in a desired timing sequence, with electric pulses having a desired duration or pattern or the like, to result in a desired pattern of contraction of the heart. In some cases of CHF, for example, it may be desirable to allow for increased filling time of the left ventricle to enhance cardiac output and ejection fraction. If the ventricle contracts too early, cardiac output will typically be less than might be achieved with a slightly delayed contraction. In some instances, it may be advantageous for the right and left ventricles to contract simultaneously, while in other cases it may be better for one ventricle to contract slightly ahead of the other. It may also be advantageous to control the timing of contractions of the right and left atria relative to one another as well as to the ventricles. Many different combinations of pacing patterns might be desirable for a variety of different patients, different activity levels and the like.

Cardiac pacing devices have certainly improved the treatment of cardiac conduction defects, but currently available devices still have certain shortcomings. For example, currently available biventricular and other pacing devices typically do not allow for significant (or in some cases any) adjustment. What little adjustment is possible typically involves a time-consuming process that is neither as objective or as accurate as would be desirable. To adjust the timing of a biventricular pacing device, for example, a cardiologist will typically fire the pacing device with a first timing sequence, while a second physician or technologist images the patient's heart during the cardiac cycle using an ultrasound device. Vector measurements are then manually made on the ultrasound images, and a computer is used to approximate cardiac performance from the vector measurements. This process may take as long as fifteen to thirty minutes, just to assess one timing sequence of the pacing device. To compare multiple timings of the pacing device may take several hours spent in a cardiology clinic, which is inconvenient for the patient as well as inefficient for the cardiologist and technician. Furthermore, even after several hours the physician only has data for a few different possible settings of the pacing device, and that data relies on the accuracy of manual measurements performed by the technician. This is just one example of the limited adjustability of today's cardiac pacing devices, but it is typical.

Additionally, once a patient leaves the clinic, any additional adjustments typically require a return visit to the cardiology clinic and another lengthy adjustment process as described above. Thus, it is often difficult to adjust a pacing device to optimize cardiac performance (cardiac output, ejection fraction, and the like) in an individual patient. Similarly, it is also difficult to optimize parameters of the pacing device itself, such as energy consumption which determines battery life, using currently available devices and methods.

Therefore, it would be desirable to have methods, apparatus and systems for enhancing cardiac pacing. Ideally, such methods, apparatus and systems would facilitate measurement of one or more cardiac characteristics and adjustment of a cardiac pacing device to allow a physician to conveniently assess performance of the pacing device at various settings. Such methods, apparatus and systems would allow a physician to select a timing sequence for a pacing device, such as a delay between firing of left-sided and right-sided leads in the heart, to achieve a desired level of cardiac performance. Also ideally, such adjustments would not only enhance cardiac pacing, and thus overall cardiac performance, but they would also enhance the performance of the cardiac pacing device itself. At least some of these objectives will be met by the present invention.

BRIEF SUMMARY OF THE INVENTION

Methods, apparatus and systems for enhancing cardiac pacing generally provide for measuring at least one cardiac characteristic, calculating at least one cardiac performance parameter based on the measured characteristic(s), and adjusting at least one functional parameter of a cardiac pacing device. In some embodiments, this adjustment step may be based on the calculated cardiac performance parameter(s), while in other embodiments the adjustment is not based on the calculated parameter. Devices may include at least one catheter (such as a multiplexed catheter with one or more sensors and/or actuators), at least one implant (such as a sensor implantable in a heart wall), or a combination of both. Various cardiac performance parameters and/or pacing device performance parameters may be weighted, and the parameters and their respective weights may be used to determine one or more adjustments to be made to the pacing device. In some instances, the adjustments are made automatically. Some embodiments may display data, such as cardiac performance parameter and/or pacing device performance parameter data, to a user via a display device. In some embodiments, a user may select which performance parameters to view on a display, assign weights to various parameters, designate which parameters will be used to determine adjustments and/or the like.

In one aspect, a method of enhancing cardiac pacing comprises: measuring at least one characteristic of a heart using one or more parameter measuring devices disposed in the heart; calculating at least one cardiac performance parameter using the at least one measured characteristic; and automatically adjusting at least one functional parameter of a cardiac pacing device. In some embodiments, the adjustment step is based on the at least one calculated cardiac performance parameter, though this is not true of all embodiments. Throughout this application, the terms "characteristic" and "parameter" are sometimes used interchangeably. In some cases, "characteristic" may mean a measured value while "parameter" may mean a calculated value. In other cases the reverse may be true, or either "characteristic" or "parameter" may be used to describe both measured and calculated values. Thus, generally, "characteristic" and "parameter" may be used interchangeably to mean "value," "amount" or the like.

In some embodiments the characteristic of the heart is measured again, after the adjusting step, the cardiac performance parameter is calculated again, and the pacing device is adjusted again. This series of steps may be repeated any number of times, and is sometimes repeated many times, to provide multiple data points to help a physician select/adjust settings for a pacing device. In some embodiments, for example, multiple data points may be displayed to the physician on a display monitor or other display device for multiple timing settings of a pacing-device. Data may be displayed as a graph, for example, such as a three-dimensional graph.

In some embodiments, measuring the at least one characteristic comprises measuring with at least one sensor device implanted in at least one wall of the heart. Alternatively, measuring the at least one characteristic may comprise measuring with at least one catheter device disposed in at least one chamber of the heart. In other embodiments, both at least one catheter and at least one implanted sensor device may be used. For example, in some embodiments a multiplexed catheter is used, and the catheter may be placed at least partially within at least one of a left ventricle and a right ventricle of the heart.

In some embodiments, measuring the at least one characteristic comprises measuring at least one of pressure, volume, blood flow velocity, blood oxygen concentration, carbon dioxide concentration, wall stress, wall thickness, force, electric charge, electric current and electric conductivity. For instance, in certain embodiments, the measuring of at least one characteristic comprises measuring at least one blood oxygen concentration in a patient having a shunt. Such characteristics may be measured in any part of the heart, such as one or more chambers and/or one or more walls of the head, or in blood vessels in and around the heart or adjacent to the heart.

In some embodiments, calculating the at least one cardiac performance parameter comprises calculating at least one of ejection fraction, cardiac output, cardiac index, stroke volume, stroke volume index, pressure reserve, volume reserve, cardiac reserve, cardiac reserve index, stroke reserve index, myocardial work, myocardial work index, myocardial reserve, myocardial reserve index, dP/dt, $d^2P/dt$, stroke work, stroke work index, stroke work reserve, stroke work reserve index, systolic ejection period, stroke power, stroke power reserve, stroke power reserve index, myocardial power, myocardial power index, myocardial power reserve, myocardial power reserve index, myocardial power requirement, ejection contractility, cardiac efficiency, cardiac amplification, valvular gradient, valvular gradient reserve, valvular area, valvular area reserve, valvular regurgitation, valvular regurgitation reserve, a pattern of electrical emission by the heart, concentration of oxygen in the cardiac vein, and a ratio of carbon dioxide to oxygen.

Adjusting the at least one functional parameter, in some embodiments, comprises adjusting at least one of a selected electrode of the cardiac pacing device to be activated, a pulse width of an activation of the cardiac pacing device, a pulse amplitude, a pulse duration, a number of pulses per one cycle of the heart, a pulse polarity, a pulse duty cycle, a timing of pulses relative to a cycle of the heart and a timing of pulses from multiple electrodes of the pacing device relative to one another.

In some embodiments, adjusting the at least one functional parameter comprises: assigning a first relative weight to a first calculated cardiac performance parameter; assigning a second relative weight to a second calculated cardiac performance parameter; and determining at least one adjustment to be made to the at least one functional parameter, based on the first and second calculated cardiac performance parameters and the first and second relative weights. Some embodiments may also include: assigning a third relative weight to a third calculated cardiac performance parameter; and determining the at least one adjustment, based on the first, second and third calculated cardiac performance parameters and the first, second and third relative weights. Alternatively, the method may further involve: determining at least one apparatus performance parameter of the cardiac pacing apparatus; assigning a third relative weight to the apparatus performance parameter; and determining the at least one adjustment, based on the first and second calculated cardiac performance parameters, the at least one apparatus performance parameter and the first, second and third relative weights. Determining the at least one apparatus performance parameter, for example, may comprise determining at least one of an energy consumption rate, a maximum current and a maximum voltage of the cardiac pacing apparatus.

Some embodiments also involve accepting at least one command from the user, the command assigning a relative weight to at least one of the cardiac performance parameters, wherein adjusting the at least one functional parameter comprises determining an adjustment to be made to the at least one functional parameter based on the at least one cardiac performance parameter and the assigned relative weight of each cardiac performance parameter. Such methods may further include accepting an additional command from the user, the additional command assigning a relative weight to at least one apparatus performance parameter, wherein adjusting the at least one functional parameter comprises determining the adjustment based on the at least one cardiac performance parameter, the at least one apparatus performance parameter and the assigned relative weights of each.

Some embodiments involve providing at least one calculated cardiac performance parameter to a user in the form of data. For example, the data may be provided as one or more images on a display monitor. Some embodiments also include accepting at least one command from the user, the command designating one or more of the calculated cardiac performance parameters to be provided to the user.

In another aspect, apparatus for enhancing cardiac pacing includes at least-one measuring device for measuring at least one characteristic of a heart and a processor coupled with the at least one measuring device for calculating at least one cardiac performance parameter based on the at least one measured characteristic, determining at least one adjustment to be made to a cardiac pacing device, and transmitting the at least one adjustment to the cardiac pacing device. As mentioned above, the at least one measuring device may comprise at least one sensor implantable within at least one wall of the heart. For example, the at least one implantable sensor may include at least one of a pressure sensor, a volume sensor, a dimension sensor, a temperature sensor, a thermal sensor, an oxygen sensor, a carbon dioxide sensor, an electrical conductivity sensor, an electrical potential sensor, a pH sensor, a chemical sensor, a flow rate sensor, an optical sensor, an acoustic sensor, a hematocrit sensor and a viscosity sensor.

In other embodiments, the at least one measuring device comprises at least one catheter positionable within at least one chamber of the heart. Sometimes, for example, the catheter comprises at least one multiplexed catheter. In some embodiments, the multiplexed catheter includes at least one sensor selected from the group consisting of pressure sensors, volume sensors, dimension sensors, temperature sensors, thermal sensors, oxygen sensors, carbon dioxide sensors, electrical conductivity sensors, electrical potential sensors, pH sensors, chemical sensors, flow rate sensors, optical sensors, acoustic sensors, hematocrit sensors and viscosity sensors. A multiplexed catheter may additionally or alternatively include at least one actuator, the at least one actuator performing a function selected from the group consisting of providing an electrical current or voltage, setting an electrical potential, generating a biopotential, pacing a heart, heating a substance or area, inducing a pressure change, releasing or capturing a material, emitting light, emitting sonic or ultrasound energy and emitting radiation. Of course, the at least one measuring device may include any combination of catheters and implantable sensors. In some embodiments, combinations of sensors and various electronics, sensors and actuators, or the like may be included on one chip device.

In some embodiments, the processor determines the at least one adjustment by assigning a relative weight to at least one of the cardiac performance parameters and calculating the adjustment based on the cardiac performance parameters and the relative weights assigned to each. Optionally, the processor may receive at least one cardiac pacing device performance parameter from the cardiac pacing device, and wherein the processor further assigns an additional relative weight to at least one of the device performance parameters and calculates the at least one adjustment based on the cardiac performance parameters, the device performance parameters, and the relative weights assigned to each. In some embodiments, the processor is coupled with the cardiac pacing device to allow the processor to automatically adjust one or more functional parameters of the device. Alternative, the processor may transmit the at least one adjustment to the cardiac pacing device via a wireless connection.

In some embodiments, the processor is couplable with a display device such that the processor transmits at least one of the cardiac performance parameters to the display device for viewing by a user. Optionally, the processor may further transmit at least one cardiac pacing device performance parameters to the display device for viewing by a user. In these or other embodiments, the processor may receive one or more commands from the user, the commands selected from the group consisting of a selection of one or more cardiac performance parameters and pacing device performance parameters to be displayed on the device, a selection of one or more cardiac performance parameters and pacing device performance parameters to be used by the processor to calculate the at least one adjustment to the cardiac pacing device, and a selection of a relative importance to be assigned to at least one of the cardiac performance parameters and pacing device performance parameters. The processor may then calculate the at least one adjustment based at least in part on the one or more commands from the user. In some embodiments, the apparatus further comprises input means for allowing the user to input one or more commands to the processor. Some embodiments further include a cardiac pacing device coupled with the processor for applying electrical stimuli to the heart.

In yet another aspect, a system for enhancing cardiac pacing includes: a cardiac pacing device; at least one measuring device for measuring at least one characteristic of a heart; and a processor coupled with the at least one measuring device and the cardiac pacing device, wherein the processor calculates at least one cardiac performance parameter based on the at least one measured characteristic, determines at least one adjustment to be made to the cardiac pacing device, and transmits the at least one adjustment to the cardiac pacing device. Optionally, the system may further comprise a display device coupled with the processor for providing data to a user, wherein the processor transmits data pertaining to at least one of the calculated cardiac performance parameters to the display device. The processor may further transmit at least one cardiac pacing device performance parameter to the display device for viewing by a user. As described above, the system may include any suitable combination of catheters and/or implantable sensors. Any of the optional elements described above in relation to apparatus of the invention may also be applied to systems of the invention.

BRIEF DESCRIPTION OF THE DRAWINGS

FIG. 5 is a cross-sectional view of a heart with multiple sensor devices implanted in various walls of the heart according to an embodiment of the present invention.

FIG. 5A is a diagram of a circuit which may be used as part of an embodiment of the present invention.

DETAILED DESCRIPTION OF THE INVENTION

Figure 1:
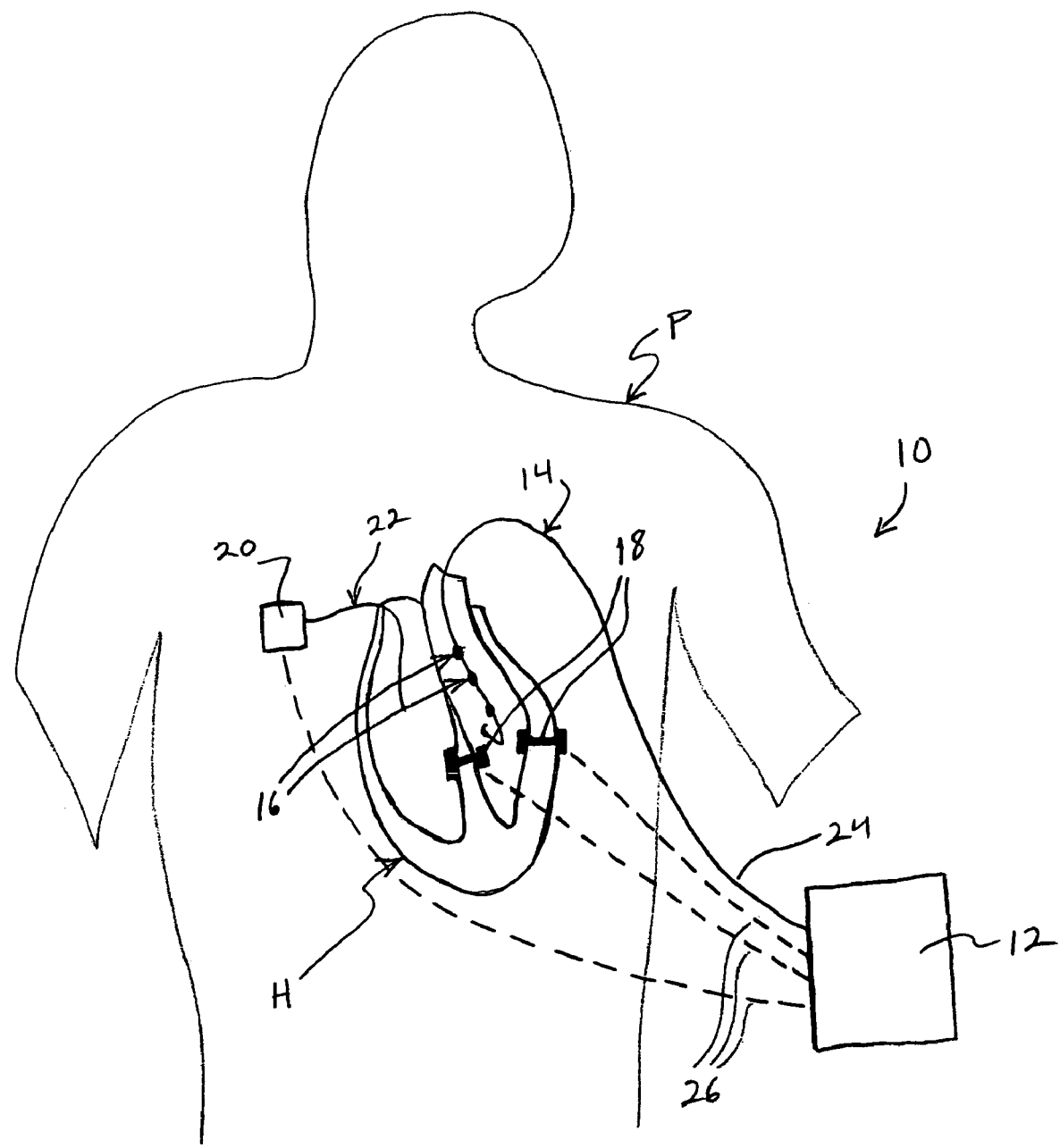
FIG. 1 illustrates a system for enhancing cardiac pacing constructed in accordance with principles of the present invention.

Methods, apparatus and systems for enhancing cardiac pacing generally provide for measuring at least one cardiac characteristic, calculating at least one cardiac performance parameter based on the measured characteristic(s), and adjusting at least one functional parameter of a cardiac pacing device. In some embodiments, the cardiac characteristic is then measured again, after the adjustment to the pacing device, the performance parameter is calculated again, and the pacing device is adjusted again. This series of adjustments, measurements and calculations may be performed any number of times, to result in multiple data points that can then be used by a physician to choose/adjust timing characteristics of the pacing device.

Devices may include at least one catheter (such as a multiplexed catheter with one or more sensors and/or actuators), at least one implant (such as a sensor implantable in a heart wall), or a combination of both. Various cardiac performance parameters and/or pacing device performance parameters may be weighted, and the parameters and their respective weights may be used to determine one or more adjustments to be made to the pacing device. In some instances, the adjustments are made automatically. Some embodiments may display data, such as cardiac performance parameter and/or pacing device performance parameter data, to a user via a display device. In some embodiments, a user may select which performance parameters to view on a display, assign weights to various parameters, designate which parameters will be used to determine adjustments and/or the like.

In some exemplary descriptions below the term "cardiac characteristic" generally refers to any measurable characteristic of a heart. For example, cardiac characteristics measurable with methods and apparatus of the invention include, but are not limited to, pressure, volume, blood flow velocity, blood oxygen concentration, carbon dioxide concentration, wall stress, wall thickness, force, electric charge, electric current and electric conductivity. Such cardiac characteristics may be measured using one or more sensors on one or more measuring devices, such as a catheter and/or an implantable sensing device. Examples of sensors may include, but are not limited to a pressure sensor, a volume sensor, a dimension sensor, a temperature sensor, a thermal sensor, an oxygen sensor, a carbon dioxide sensor, an electrical conductivity sensor, an electrical potential sensor, a pH sensor, a chemical sensor, a flow rate sensor, an optical sensor, an acoustic sensor, a hematocrit sensor and a viscosity sensor. To measure some cardiac characteristics, it may be advantageous to also induce a change in a heart. Thus, some devices of the invention may include an actuator for functions such as but not limited to providing an electrical current or voltage, setting an electrical potential, generating a biopotential, pacing a heart, heating a substance or area, inducing a pressure change, releasing or capturing a material, emitting light, emitting sonic or ultrasound energy and emitting radiation.

Also in some descriptions below, the phrase "cardiac performance parameter" generally refers to any parameter for describing performance of a heart. Often in embodiments of the present invention, cardiac performance parameters are calculated or otherwise derived from measured cardiac characteristics and from one or more algorithms, functions, formulas and/or the like which relate the measured characteristics. Examples of cardiac performance parameters which may be used in methods of the present invention include, but are not limited to, ejection fraction, cardiac output, cardiac index, stroke volume, stroke volume index, pressure reserve, volume reserve, cardiac reserve, cardiac reserve index, stroke reserve index, myocardial work, myocardial work index, myocardial reserve, myocardial reserve index, stroke work, stroke work index, stroke work reserve, stroke work reserve index, systolic ejection period, stroke power, stroke power reserve, stroke power reserve index, myocardial power, myocardial power index, myocardial power reserve, myocardial power reserve index, myocardial power requirement, ejection contractility, cardiac efficiency, cardiac amplification, valvular gradient, valvular gradient reserve, valvular area, valvular area reserve, valvular regurgitation and valvular regurgitation reserve. Measurement of such cardiac performance parameters is described more fully below, but for further detail reference may be made to U.S. Provisional Patent Application Ser. No. 60/442,441, which was filed on Jan. 24, 2003, entitled "Methods and Systems for Measuring Cardiac Parameters," is assigned to the assignee of the present invention, and is hereby incorporated fully by reference.

"Cardiac pacing device functional parameters," or simply "functional parameters," generally refers to any parameters that describe the functioning of a cardiac pacing device and that may be adjusted. Thus, the phrase "adjustable parameters" may occasionally be used synonymously with "functional parameters." Examples of functional parameters of a cardiac pacing device which may be adjusted include, but are not limited to, a selected electrode of the cardiac pacing device to be activated, a pulse width of an activation of the cardiac pacing device, a pulse amplitude, a pulse duration, a number of pulses per one cycle of the heart, a pulse polarity, a pulse duty cycle, a timing of pulses relative to a cycle of the heart and a timing of pulses from multiple electrodes of the pacing device relative to one another.

The phrase "cardiac pacing device performance parameters," on the other hand, generally refers to any parameters of the performance of a pacing device which describe how the device is functioning. In some instances, these device performance parameters are measurable, so that the performance of the device can be tracked. For example, some pacing device performance parameters include, but are not limited to, an energy consumption rate, a maximum current and a maximum voltage of the pacing device.

Referring now to FIG. 1, an exemplary system 10 according to an embodiment of the invention includes at least one catheter device 14 having at least one sensor 16, at least one implantable sensor 18 implantable in a wall of a heart H of a patient P, a cardiac pacing device 20 with one or more leads 22, and a processor 12 coupled to the catheter device 14, the implantable sensors 18 and the pacing device 20 via wired connections 24 and/or wireless connections 26. Any given embodiment of the system 10 may include fewer elements than are shown in FIG. 1, or may include one or more additional elements. For example, some embodiments may include one or more catheters 14 with no implantable sensors 18, other embodiments may include one or more implantable sensors 18 with no catheters 14, and any other suitable combination is contemplated within the scope of the present invention.

Catheters and other devices such as catheter 14 in FIG. 1 are described in greater detail below, but for further detail reference may be made to U.S. Provisional Patent Application Ser. No. 60/432,929, which was filed Dec. 11, 2002, entitled "Methods and Systems for Monitoring and Treating Hemodynamic Parameters," is assigned to the assignee of the present invention, and is hereby incorporated fully by reference. Implantable sensors such as implantable sensors 18 in FIG. 1 are also described in greater detail below, but for further detail reference may be made to U.S. Provisional Patent Application Ser. No. 60/442,376, which was filed on Jan. 24, 2003, entitled "Method and System for Remote Hemodynamic Monitoring," is assigned to the assignee of the present invention, and is hereby incorporated fully by reference.

As mentioned above, many changes could be made to the system 10 depicted in FIG. 1 without departing from the scope of the invention. In some embodiments, for example, a pacing device 20 having multiple leads 22 is used, such as for biventricular pacing. In other embodiments, two or more components may be combined into one device. The catheter 14 and a lead 22 may be combined on the same device, for example. As another example, catheters 14 and implantable sensors 18 may be used in any suitable combination and may be placed in and around the heart H in any suitable location (s). Regarding the location of various parts of the system 10, any suitable locations are possible. In some embodiments, for example, all parts of the system may be implantable within a patient. In other embodiments, the processor 12 is located outside the patient P and may be coupled with the other parts of the system 10 continuously or periodically for adjustments to one or more devices in the system 10.

Other devices may also be coupled with processor 12 and/or other devices shown in FIG. 1. For example, in some cases an electrocardiogram (ECG) device may be coupled with the patient P and with processor, to provide additional information to the processor 12 regarding the functioning of the patient's heart H. In another embodiment, an oxygen sensor may be coupled with the processor 12 and the patient P to enable measurement of the oxygen concentration and/or carbon dioxide concentration of the patient's breath, blood or the like. These or other embodiments may further include an external actuator device, typically coupled with the processor 12 and/or the catheter 14 for activating one or more actuation devices on the catheter to induce a change in a characteristic of the heart H. Thus, any suitable combination of devices is contemplated within the scope of the invention, and the system 10 described in FIG. 1 and following figures is provided for exemplary purposes only.

Figure 2:
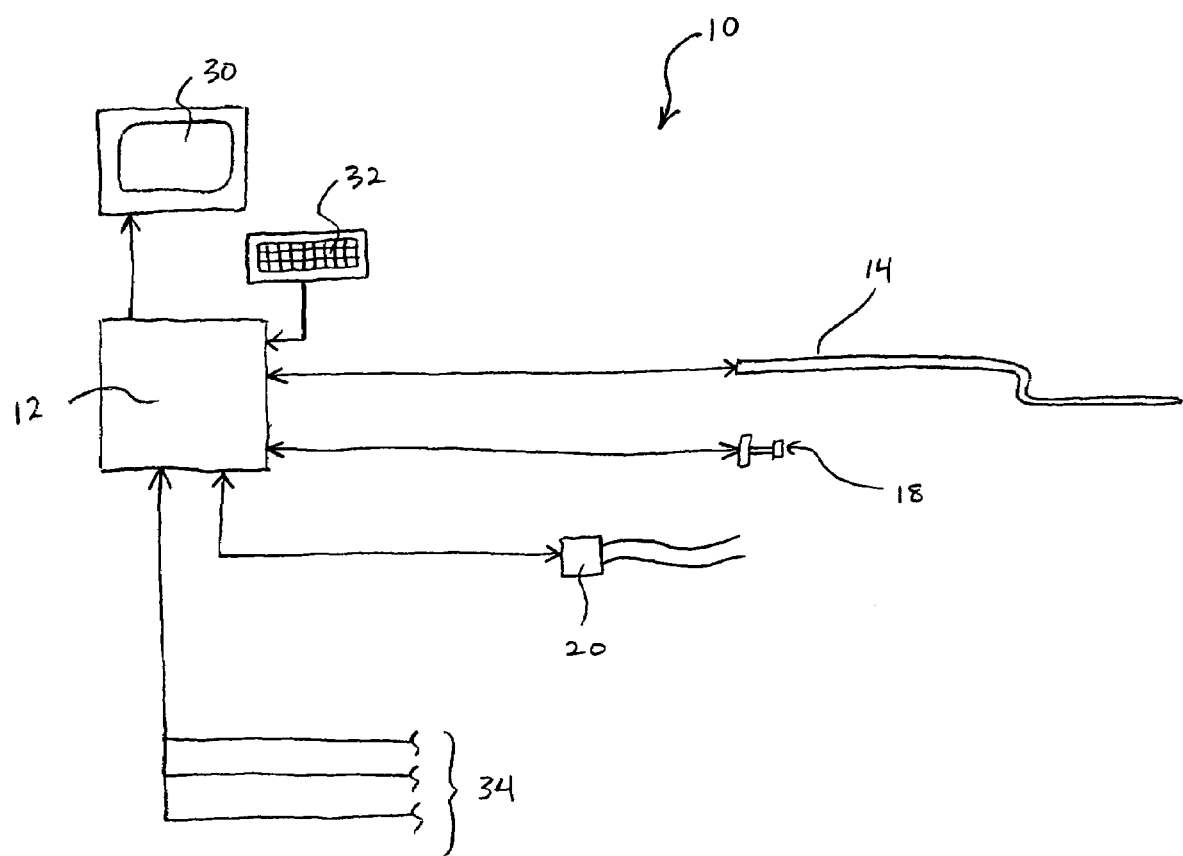
FIG. 2 is a schematic illustration of the system according to FIG. 1, including interfaces between various components of the system.

Referring now to FIG. 2, the system 10 from FIG. 1 is shown schematically, including interfaces between various components of the system 10. Processor 12 is shown coupled with a catheter 14, an implantable sensor 18, a cardiac pacing device 20, a display monitor 30 and an input device 32. In addition, as just discussed, processor 12 may also be coupled with one or more additional devices 34 through one or more additional channels. Any suitable combination of connections may be used for coupling processor 12 with the various devices shown in FIG. 2, such as wired and/or wireless connections.

The display monitor 30 and the input device 32 are optional. In some embodiments, they may be combined into one device, combined with the processor 12 or the like. Generally, the display monitor 30 receives data from the processor 12 and displays at least some of it for viewing by a user. Such data may include, for example, one or more cardiac performance parameters, one or more pacing device performance parameters, various weights that are being given to various parameters in determining whether an adjustment to the cardiac pacing device should be made, and/or the like. Any suitable display is contemplated, such as charts, tables, graphs, curves, overlapping curves, images, real-time replicated images of a heart, and/or the like. A user may use input device 32, such as a computer keyboard, an electronic notepad, or the like to input data to processor 12. Such data may include, but of course is not limited to, a selection of one or more parameters that the user desires to view on the display device, a selection of one or more parameters that the user desires to have the processor use to calculate adjustments to the pacing device 20, an assignment of a weight to one or more parameters, and/or the like. Generally, display monitor 30 may display any data and input device 32 may be used to input any data without departing from the scope of the invention.

Methods of the present invention generally include first measuring at least one characteristic of a heart using one or more of the measuring devices described above, such as the catheter 14 and/or the implantable sensor 18, using any combination of devices described in more detail below, or using any other suitable measuring device. The processor then calculates at least one cardiac performance parameter using the measured characteristic(s). This process is described more fully below. The processor then automatically adjusts at least one functional parameter of a cardiac pacing device, based on the calculated cardiac performance parameter(s).

In some embodiments, the adjustment(s) to the functional parameter(s) are determined via an algorithm or "optimization function." The optimization function comprises an equation in which selected parameters are assigned weights and the measured parameters are then compared, using their assigned weights, to arrive at one or more adjustments. For example, it may be desired to maximize stroke volume of a heart up to a set level, while also minimizing myocardial work, maximizing cardiac efficiency and minimizing the power consumption of the cardiac pacing device. Each of these goals may be assigned a weight, or "importance level," and an optimization function may be used to achieve each of these goals to the greatest extent possible at the same time. Many other combinations of such goals, parameters and the like are contemplated. In fact, any of the parameters described more fully below may be used in forming and then using an optimization function. Further, the term "optimization" is not necessarily used to mean "the best." In contrast, it is used to mean that each of a set of goals set forth in the optimization function is achieved to the greatest degree possible, based on its relative weight.

In many embodiments, one or more optimization functions, parameters to be used in calculating adjustments to the cardiac pacing device 20, weights to be given to the parameters and the like are programmed into the processor 12 before the system 10 is made available to a user. In some embodiments, the system 10 then allows the user to choose either to leave these "default settings" as they are or to choose one or more new settings. The user may be able to choose, for example, to view the parameters being used to calculate the adjustments, as well as their respective weights, on the display monitor 30. The user may then choose to select one or more additional parameters or may choose to eliminate parameters from the optimization function. Additionally or alternatively, the user might be able to assign different relative weights to one or more of the parameters. In some embodiments, the user may set one or more minimum and/or maximum levels for one or more parameters, and if a parameter exceeds a selected maximum or falls below a selected minimum, an alarm may sound or some other measure may be taken by the system 10 to correct the situation or alert the user or the patient.

The user may make these selections, for example, by inputting them to the processor 12 via the input device 32. Again, any combination of parameters, weights and the like is possible, and a user may be given any suitable selection of choices without departing from the scope of the invention. For example, a user may choose one set of parameters and weights in one instance, perhaps if a patient is to be engaging in a more energy intense activity, and may choose another set of parameters and weights in another instance, such as when the patient is to be sleeping. In some embodiments, multiple sets of parameters and weights may be programmed into the processor 12 so that a patient's pacing device operates somewhat differently at different times of the day, when different activities are likely being performed, and/or the like. For example a pacing device may be programmed to cycle through a full day, with varying rates and patterns of firing at different times, based on what activity the patient is doing. Thus, the system 10 makes customization of a patient's cardiac pacing via a pacing device possible.

As mentioned above, in some embodiments it is also possible to include one or more cardiac pacing device performance parameters in the optimization function used to determine adjustments to the pacing device 20. Thus, it may be built into the system 10 and/or the user may designate that one of the goals of the system 10 is to minimize energy consumption of the system, for example, so as to prolong battery life of the pacing device 20. Such a goal, of course, would have an assigned weight, so that minimizing energy consumption would be weighed against the goals based on enhancing cardiac function. Again, any combination of parameters relating to cardiac performance and device performance, as well as any combination of relative weights for those goals, is contemplated within the scope of the invention. In some embodiments, a user may be able to set one or more minimum or maximum levels for specific variables.

Figure 3:
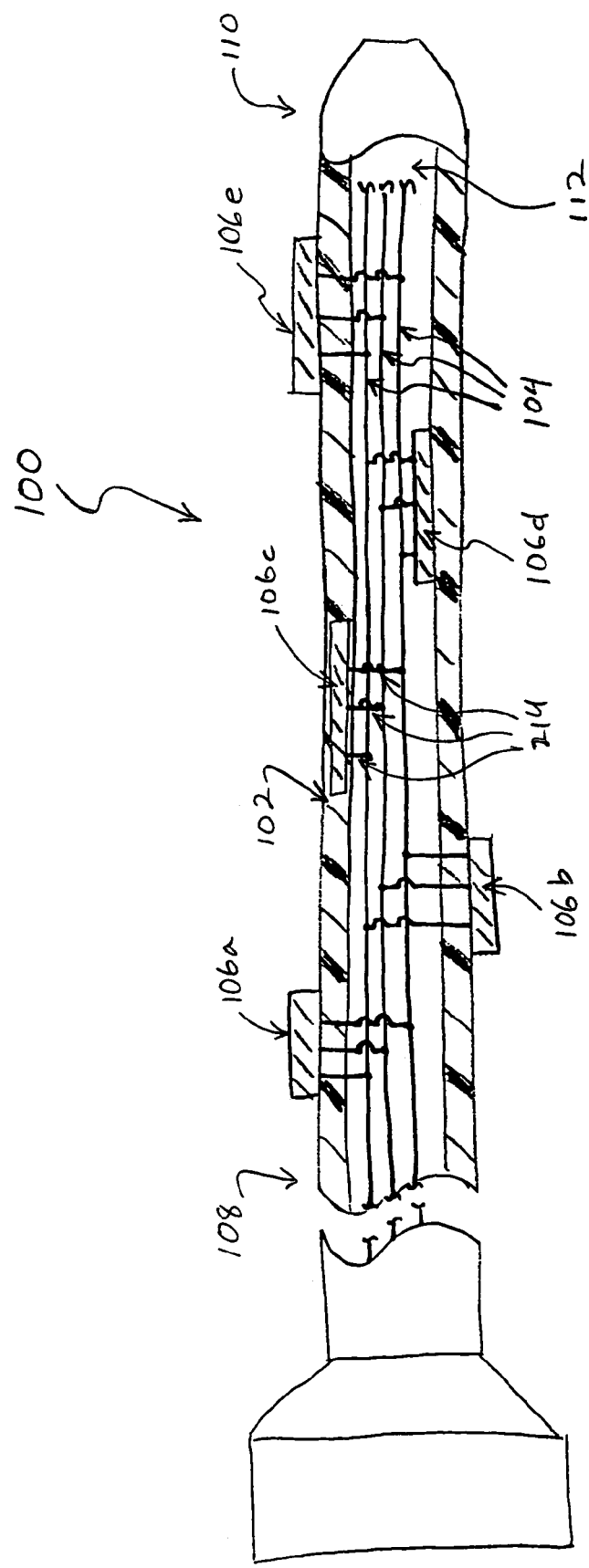
FIG. 3 is a schematic illustration of a multiplexed medical carrier, in the form of an intraluminal catheter, which may be used as part of an embodiment of the present invention.

Turning now to FIG. 3, a schematic illustration shows a multiplexed medical carrier in the form of an intraluminal catheter 100 such as may be used as part of the present invention. In various embodiments other multiplexed medical carriers may be used, such as three-dimensional grid-like carrier or any other suitable carrier. Again, for details in addition to those set forth below, reference should be made to U.S. Provisional Patent Application Ser. No. 60/432,929, entitled "Methods and Systems for Monitoring and Treating Hemodynamic Parameters," which was previously incorporated by reference.

The multiplexed medical carrier 100 of the present invention suitably includes a body 102, multiple electrical conductors 104 disposed in body 102, and multiple, separately addressable effectors 106a–e, which may be disposed at distributed locations within body 102, in a lumen 112 of body 102, and/or on an exterior surface of body 102. In any given embodiment, many variations may be made in the size or configuration of body 102, in the number and type of electrical conductors 104, in the number and type of effectors 106a–e and/or the like. Thus, the embodiment shown in FIG. 3 and described further below is merely one exemplary embodiment and should not be interpreted to limit the scope of the invention as set forth in the claims.

Body 102 of multiplexed medical carrier 100 may have any suitable shape, size, configuration, dimensions and the like. In some embodiments, as in FIG. 3, body 102 comprises an elongate catheter body having a proximal end 108 and a distal end 110 and defining a central lumen 112. In addition to central lumen 112, in some embodiments body 102 includes one or more intramural lumens (not shown), which run longitudinally within body 102 and may house one or more electrical conductors 104, a conductive gel or fluid and/or other components of multiplexed carrier 100. (Generally, the phrase "within body 102" means within the wall of body 102. A location within central lumen 112 formed by body 102 will be referred to as "in central lumen 112.") In other embodiments, body may comprise a flat surface, with effectors being disposed along the surface and with conductors disposed along adjacent flat surfaces.

In many embodiments, body 102 may comprise a catheter body adapted for intraluminal introduction into a target body lumen or other body structure, such as vasculature or the heart. The dimensions, materials and other physical characteristics of body 102 will vary significantly depending on the body structure to be accessed and monitored. For example, one or more portions of body 102 may be flexible while one or more other portions may be relatively rigid. Body 102 may include a guidewire lumen configured for over-the-wire or rapid exchange introduction, in various embodiments. Catheter bodies intended for intravascular introduction may have a length in the range from 50 cm to 200 cm and an outer diameter in the range from 1 French to 12 French (0.33 mm: 1 French). Bodies 102 will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, the heart, or any other desired location by conventional techniques.

In embodiments in which body 102 comprises an elongated body, such as an intravascular or other intraluminal catheter, electrical conductor(s) 104 extend axially from a distal location at or near the distal tip of the elongated body to a proximal connection, typically within a proximal hub on the catheter or other elongated body 102. In such cases, effectors 106 will typically be axially spaced-apart, although they may also be circumferentially spaced apart under certain circumstances. Such catheters may comprise any suitable number of effectors, such as from two effectors 106 to 100 effectors 106, typically comprising from 4 effectors 106 to 40 effectors 106, and more typically comprising from 4 effectors 106 to 12 effectors 106.

Electrical conductors 104 generally comprise conductors running axially along all or a portion of the length of body 102. Conductors 104 may comprise thin, elongate wires, a conductive sheath or mesh disposed within or on a surface of body 102, or the like. In one embodiment, only one electrical conductor 104 is used and a conductive fluid or gel in central lumen 112 or an intramural lumen acts as a ground. More commonly, however, multiplexed medical carrier 100 includes two, or preferably three, electrical conductors 104. In some embodiments, each electrical conductor 104 is isolated. In one embodiment, body 102 may comprise three or more intramural lumens and each electrical conductor 104 may be housed in a separate intramural lumen. Furthermore, each electrical conductor 104 typically performs a unique function. In an embodiment having three conductors 104, for example, one conductor 104 comprises a ground conductor, one comprises a power conductor and one comprises a data conductor. A ground conductor generally acts as a conventional electrical grounding mechanism, to return electrical current to the proximal end 108 of multiplexed carrier 100. A power conductor provides energy to one or more effectors 106a–e and a data conductor may transmit data to and/or from one or more effectors 106a–e. As mentioned previously, three electrical conductors 104 is described as an exemplary embodiment only. Various other embodiments may include, one, two or more than three conductors 104. Some embodiments may even include no conductors 104, for example if wireless RF communication is used.

In a given embodiment, multiplexed medical carrier 100 may include one effector 106, two effectors, five effectors (as shown in FIG. 3) or any other suitable number of effectors 106a–e. Effectors 106a–e, may be of any suitable size and configuration and may be disposed within carrier body 102 (as effector 106c) on an interior surface of body 102 (as effector 106d) and/or on an exterior surface of body 102 (as effectors 106a, b and e). Furthermore, effectors 106a–e may be positioned at any suitable locations relative to the longitudinal length of body 102. For example, it may be advantageous to dispose effectors 106 along the length of carrier 100 so as to measure one or more parameters in two adjacent chambers of the heart simultaneously. Any suitable combination of numbers, types, sizes and placements of effectors 106 is contemplated within the scope of the invention.

Each effector 106a–e is coupled with each electrical conductor 104 via a lead 214. Medical carriers 100 of the present invention, such as the catheter in FIG. 1, are referred to as "multiplexed" because multiple, separately addressable effectors 106a–e are coupled with a single set (or "network") of electrical conductors 104. For example, in one embodiment all effectors 104 would be coupled with a common ground conductor, a common data conductor and a common power conductor. Such multiplexing provides for convenient use of multiple effectors 106 on one carrier 100, without requiring a separate set of electrical conductors 104 for each effector 104. Using separate sets of conductors for each effector 106 on the other hand, as with currently available devices, limits the number of possible effectors 106 due to;. constraints of size and maneuverability of the catheter.

Figure 4:
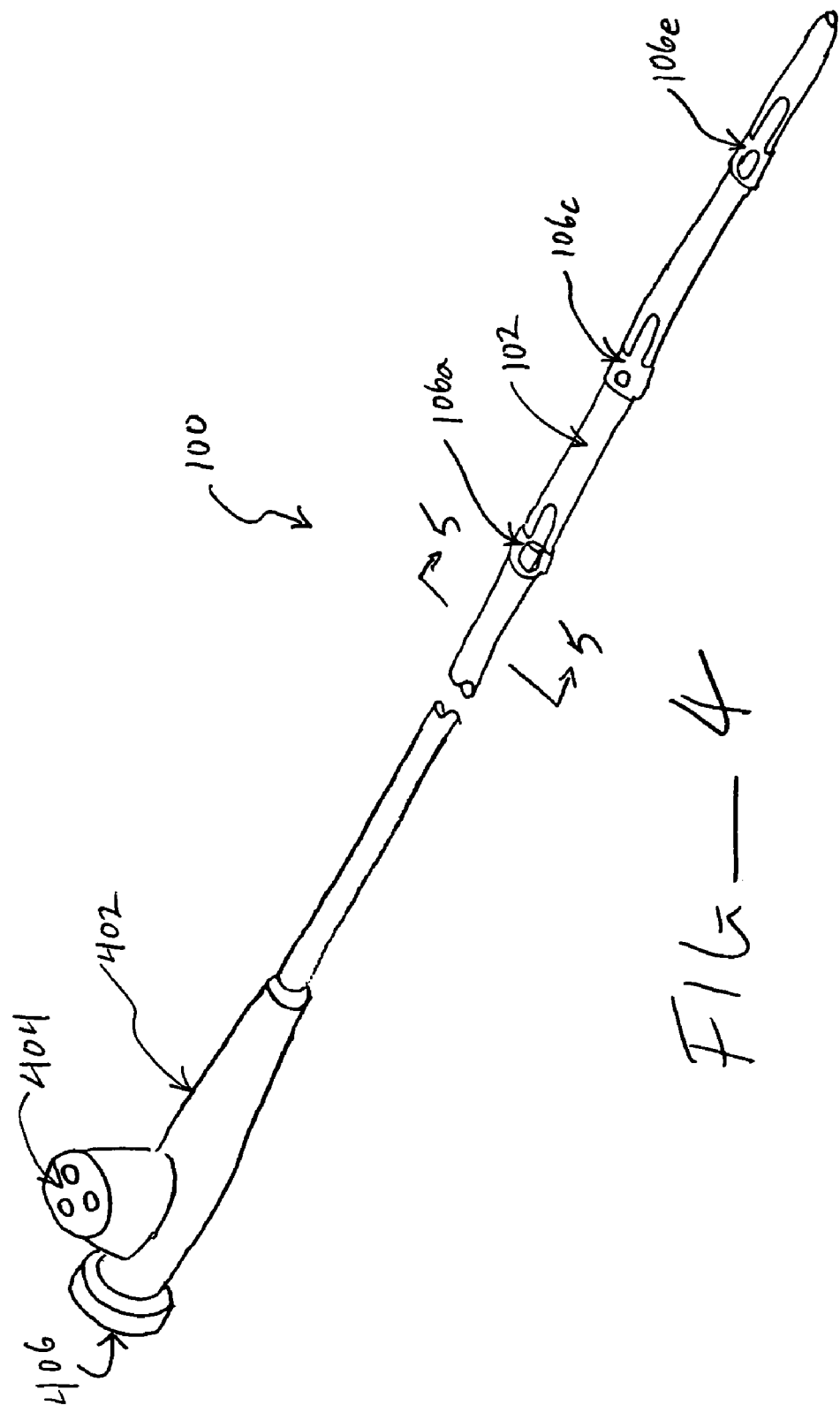
FIG. 4 is a perspective view of an intravascular or intracardiac catheter having multiple sensors which may be used as part of an embodiment of the present invention.

With reference now to FIG. 4, multiplexed medical carrier 100 is shown in perspective view. Carrier 100 may generally include body 102 coupled at its proximal end with a handle 402. As previously described, body 102 may include multiple effectors 106a–c disposed at dispersed locations wholly or partially on its outer surface. Handle 402 may include any suitable means for holding, manipulating, activating or otherwise using multiplexed carrier. For example, handle 402 may suitably include one or more electrical connections 404 and one or more fluidic connections.

As previously mentioned, the multiplexed carrier 100 in the form of an intraluminal catheter is only one of many suitable devices which may perform the functions of the catheter 14 shown in FIGS. 1 and 2 and described as an optional component of the system 10. The above description was thus provided for exemplary purposes only and should not be interpreted to limit the scope of the invention to one including a multiplexed carrier 100 or in any other way.

As mentioned above, in some embodiments pacing device 20 of system 10 may include two of more pacing leads 22. Each pacing lead 22 may have only one electrode or may have two or more electrodes. In some embodiments, multiple electrodes on a single pacing lead may be multiplexed, as described above in the context of the multiplexed catheter and FIGS. 3 and 4. Thus, in contrast to currently available pacing devices which have only one electrode per lead, pacing devices 20 of the present invention may optionally include one or more leads 22 having multiple electrodes. In one embodiment, such a multiplexed pacing device 20 might include, for example, one, two or three wires running the length of each pacing lead. A chip may be attached to the wire(s) at various points along the lead for decoding multiplexed signals and determining if and when to pulse an electrode coupled with the chip. Each chip may have either it's own "address" or a dedicated frequency for communicating information.

In one embodiment, for example, pacing device 20 may include a one-wire multiplex system. In such a pacing device 20, a very low level current might be used to send data to each of multiple electrodes (and possibly a returning signal from each electrode, as well, to validate the functionality of each electrode). In some embodiments, the low current signal may be transmitted on a high frequency carrier, to enhance the signal-to-noise ratio for low current level communications. A higher current could then be used to pace the heart. In the one-wire system, both currents (communication and pacing) may flow through the electrode into the myocardium, through the body tissue, and return to the pacing device's electrically conductive exterior. Thus, a high value capacitor may be placed on each chip between the pacing wire and the electrode that contacts the blood/tissue. Charge delivered by the pacing control system will be stored by that capacitor, generating a voltage between the electrode and the wire contact. This voltage may be used to power the electronics on the pacing chip. The communication signal may also be transmitted as a time-varying signal between the tissue-contacting electrode and the wire contact.

With reference now to FIG. 5A, in one embodiment, two rectifiying bridges 201, 202 are connected in parallel with a pacing wire 200. The output of each bridge 201, 202 is in turn connected to a capacitor C1, C2. In FIG. 5A, RL represents the equivalent load of the control electronics. The product RL*C1 is much greater than R2*C2. Thus V1, the supply voltage for each chip, doesn't change much when there is a temporary pause in the AC voltage appearing on the pacing wire. On the other hand, V2 has a much faster time-constant, and when the AC signal is turned off even very briefly, V2 quickly goes to zero. Thus, V2 is the voltage that filters the communication signal from the AC supply, and V1 is the supply voltage for the on-chip electronics. When the pacing chip receives a signal instructing it to allow its electrode to "fire," it turns a high-current transistor on board it's chip "on," allowing a high current to flow from the pacing lead to the blood/tissue without a large voltage drop across the pacing chip. In some embodiments, each electrode may have a dedicated frequency. When that frequency appears on the pacing lead, a filter on the pacing chip may detect the presence of that frequency and activate its high-power transistor. Typically, the pacing pulse consists of a DC pulse for at least around 1 ms duration, so a carrier frequency of around 10 MHz may be added to the pulse without changing its bio-electric effect.

Referring now to FIG. 5, examples of implantable sensors 18 are shown implanted in multiple locations in the walls of the heart H. Of course, various embodiments of the system 10 may use different combinations or locations of sensors 18, may use only one sensor 18 or may use no implanted sensor at all, but instead only one or more catheter devices. FIG. 5 and the following description are thus provided for exemplary purposes only. As mentioned above, additional description of such implanted sensors 18 may be found in U.S. Provisional Patent Application Ser. No. 60/442,376, entitled "Method and System for Remote Hemodynamic Monitoring," which was previously incorporated by reference.

The implantable cardiac sensors 18 may take a variety of forms, with exemplary forms shown as 18a–18d. In the illustrated embodiments 18a–18d, the sensor devices comprise a frame or platform which is attached to the myocardium or other surface of the heart H as well as one or more sensors capable of measuring particular cardiac parameters, as described in more detail below. The frames or platforms of the sensor devices 18 may take a variety of forms, including a simple patch, disk, mesh, membrane, or other surface which is attached to a myocardial or other heart surface, as shown at 18a. Such simple platforms may be sutured, tacked, stapled, or screwed into their desired target locations. The target locations may be endocardial (as shown), or may be epicardial, on a septum, or elsewhere. The sensors on the platform will be arranged to measure either myocardial parameters, typically being directed inwardly toward the myocardial tissue, or may be intended to measure the "cardiac" characteristics such as blood pressure or other parameters within a heart chamber or elsewhere.

In addition to the simple surface-mounted platforms (as illustrated in 18a), the implantable cardiac sensor devices may include platform pairs mounted on opposite surfaces of a heart wall, as shown at 18b. In particular, the two platforms of device 18b need not be mechanically connected, but will typically be arranged directly across from one another or some other predetermined pattern relative to one another on the opposite surfaces of the heart wall (including septums). Usually, the two platforms of the device 18b will be intended to interact in some predetermined fashion.

Sensors 18 may also penetrate a heart wall or septum (referred to collectively herein as "myocardial walls"). Sensor device 18c comprises a central shaft or tether 130 (FIG. 6) having buttons or platforms at each end. A particular structure for such a cardiac sensor is described in connection with FIG. 6 below.

The fourth exemplary implantable cardiac sensor device 18d is similar to 18c, except that the two buttons or platforms are generally equal size on either side of the myocardial wall. Such equal or at least enlarged platforms allow the device to apply tension which may be useful in a variety of particular measurements.

Figure 6:
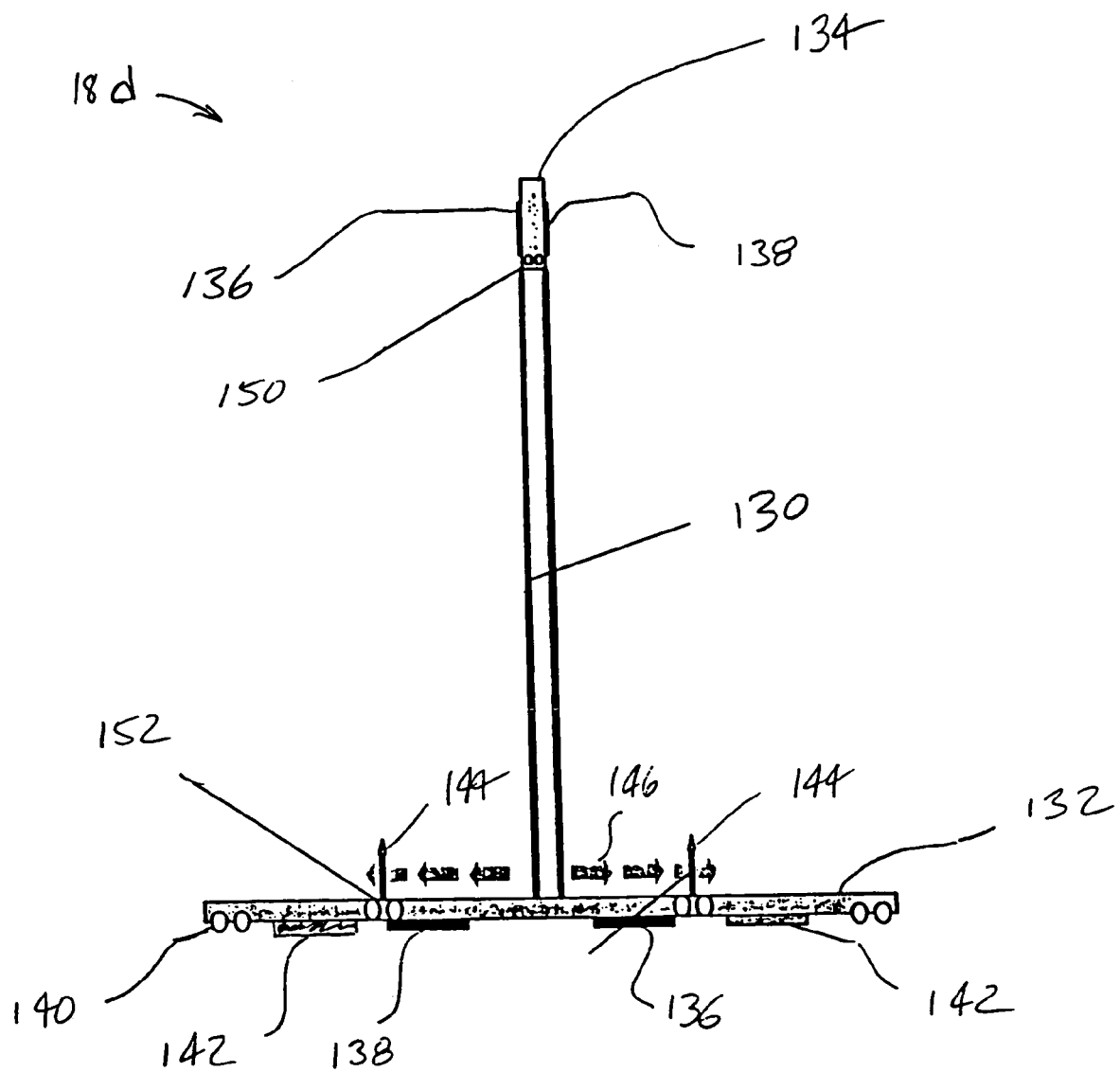
FIG. 6 illustrates an exemplary implantable sensor structure carrying multiple sensors which may be used as part of an embodiment of the present invention.

Referring now to FIG. 6, the implantable cardiac sensor device 18d comprises a first or base platform 132 and a second or remote platform 134 located at opposite ends of the shaft or tether 130. The shaft or tether 130 will usually include flexible wires, optical waveguides, or other elements for interconnecting sensors located on the respective platforms 132 and 134. The shaft or tether itself may be rigid or flexible, optionally being at least somewhat elastic to permit relative movement of the first and second platforms 132 and 134 as the myocardial tissue expands and contracts during the cardiac cycle.

Each of the platforms 132 and 134 will carry one or more sensors intended to measure physiologic parameters or characteristics, as generally set forth above. For example, either of the platforms 132 or 134, or both, may carry oxygen sensors 136, pressure sensors 138, coils 144 receiving power and/or data and optionally transmitting data back to the repeater or external controller interface. Additionally, the base platform 132 may have a circular orthogonal, or other stain gauge 142 imprinted on the surface thereof. The strain gauge 142 will thus permit measurement of lateral deflection of the myocardial tissue in which the sensor device 102d is implanted. Usually, the platform will include prongs 144 which secure the base platform 142 in tissue so that as the tissue expands in the direction of arrows 146 (or contracts in the opposite direction), the strain gauge 142 can measure the deformation and thus the expansive force being generated by the tissue at the location where the sensor is implanted. Additionally, sensor 102d can include inductance coils 150 and 152 which permit tracking elongation of the sensor along the axis of shaft or tether 130. Tracking elongation permits calculation of the expansive force of the myocardial tissue in the direction normal to the tissue plane. The particular uses of the data collected by the sensor 102d (as well as all other sensor described herein) will be described in more detail below in connection with the calculation of specific cardiac performance values.

It should be appreciated that the sensor 18d is illustrated to work by wireless transmission, either with an implanted or wearable repeater or directly with the external controller. Information and power to the sensor 18d, however, could also be obtained through wired connections, either with a repeater or directly with an intravascular catheter. In a particular embodiment, the repeater could be part of a cardiac pacing system wherein the pacing leads provide for wired connections to the implanted cardiac sensor devices 18.

Particular implantable sensors for directly measuring cardiac and myocardial characteristics may take a wide variety of forms, including many conventional sensor constructions which are known and described in the patent and medical literature. Some examples of sensors include, but are not limited to, oxygen sensors, carbon dioxide sensors, mechanical sensors for sensing myocardial elasticity and/or contractility and/or the like.

Whether one or more catheters 14 (such as the multiplexed carrier 100), one or more implantable sensors, or some combination of both is used as part of the present invention, in various embodiments a variety of cardiac characteristics may be measured and a variety of cardiac performance parameters may then be calculated by processor based on the measured characteristics. Exemplary cardiac characteristics that can be directly measured using catheters and/or implanted and other sensors according to the present invention are listed in Table I below.

TABLE I

| Directly Measured Physiologic Parameter | Symbol |
| --- | --- |
| Pressure | P |
| Displacement | D |
| Force | F |
| Oxygen Concentration | O2 |
| Pulse Rate | BP |
| Quantity Air Breathed | Q |
| Volume | V |
| Myocardial Elasticity | ME |

A variety of sensors are available for measuring the parameters set forth in Table I. Preferred are those sensors which can be miniaturized to fit on the platforms described above which are incorporated in the implantable sensor devices of the present invention. As noted previously, the platforms will preferably have areas in the range from 1 mm$^2$ to 200 mm$^2$, preferably 2 mm$^2$ to 100 mm$^2$, and often from 5 mm$^2$ to 50 mm$^2$. The large platform sizes will typically be used for radio frequency (RF) communication with a repeater or in some instances with a transmitter/receiver located external to the patient. Typically, repeaters will reside on the right side of the heart or in the pericardium. Smaller platform sizes will typically be used for sensor placement, e.g. for sensors intended for placement on or in the left-heart epicardium. The sensors will preferably have footprints which are less than these available areas, typically being from 0.001 mm$^2$ to 1 mm$^2$, preferably from 0.01 mm$^2$ to 0.1 mm$^2$. Such size limitation will, of course, not apply to the sensors needed to measure the quantity of air breathed, the oxygen concentration the air breathed, external pulse rate, or the like. For example, one or more sensors may be used in some embodiments to measure ambient pressure or a proxy for ambient pressure, which may be used for various purposes such as for comparison with a measured pressure inside a heart chamber. In some embodiments, such sensors may be implanted in the patients, such as under the skin near the clavicle or at another suitable location, while in other embodiments such sensors may reside outside the patient. Any given pressure in one or more heart chambers may then be determined by measuring the absolute pressure(s) in the chamber(s), measuring ambient pressure via the ambient pressure (or proxy) sensor, and subtracting the ambient pressure from the absolute pressure.

Based on cardiac characteristics measured by one or more multiplexed catheters, for example, many possible cardiac performance parameters may be calculated. These parameters and methods for calculating them are described below, but for further detail reference may be made to U.S. Provisional Patent Application Ser. No. 60/442,441, entitled "Methods and Systems for Measuring Cardiac Parameters," previously incorporated by reference.

In addition to many known cardiac performance parameters, such as cardiac output and ventricular pressure, catheter devices and methods of the present invention provide for measurement and/or calculation of additional parameters that have not been previously measured. A table (Table II) summarizing some of these is presented below. Others parameters may also be measured or calculated, such as the inverse of a parameter or the use of the parameter for a specific chamber or valve. Thus, the following table is not exhaustive.

TABLE II

| Name | Variable | Equation | Description |
|---|---|---|---|
| Left Ventricle Pressure | LVP | Measured directly | Gauge pressure in Left Ventricle |
| Left Ventricular Volume | LVV | Measured directly | Volume of left ventricle |
| End diastolic volume | EDV | Measured directly | Volume of chamber when volume is maximum |
| End systolic volume | ESV | Measured directly | Volume of chamber when volume is minimum |
| End diastolic pressure | EDP | Direct measurement | Gauge Pressure in chamber when volume is maximum |
| End systolic pressure | ESP | Direct measurement | Gauge Pressure in chamber when volume is minimum |
| Aortic Pressure | AOP | Direct measurement | Gauge Pressure in aorta just distal to Aortic Valve |
| Ejection Fraction | EF | (EDV − ESV)/EDV | Describes the percentage of blood ejected from a chamber (usually LV) during a cycle |
| Cardiac Output | CO | Fick or dilution or $k * \int \text{Velocity} * HR$ | Total amount of blood pumped by the heart per minute |
| Cardiac Index | CI | CO/BSA | Cardiac output normalized by Body Surface Area |
| Stroke Volume | SV | CO/HR or $k * \int \text{Velocity}$ | Net amount of blood ejected into aorta in one cycle. Measured either from cardiac output or from the integral of calibrated blood velocity during a cycle. |
| Stroke Volume Index | SVI | SV/BSA | Stroke volume normalized by Body Surface Area |
| Pressure Reserve | PR | d(LVESP)/d(LVEDP) | Marginal change in end systolic pressure due to a marginal change in end-diastolic pressure |
| Volume Reserve | VR | d(LVESV)/d(LVEDV) | Marginal change in end systolic volume due to a marginal change in end-diastolic volume |
| Cardiac Reserve | CR | d(CO)/d(LVEDP) | Marginal increase in cardiac output due to a marginal increase in LVEDP |
| Cardiac Reserve Index | CRI | d(CI)/d(LVEDP) | Cardiac Reserve normalized by Body Surface Area |
| Stroke Reserve | SR | d(SV)/d(LVEDP) | Marginal increase in stroke volume due to a marginal increase in LVEDP |
| Stroke Reserve Index | SRI | d(SVI)/d(LVEDP) | Stroke Reserve normalized by Body Surface Area |
| Myocardial Work | MyW | $\int_{dV/dt<0} P\,dv - \int_{dV/dt>0} P\,dv$ | Work performed by myocardial tissue during a single cycle |
| Myocardial Work Index | MyWI | MW/BSA | Myocardial work normalized by Body Surface Area |
| Myocardial Reserve | $M_yR$ | d(MW)/d(LVEDP) | Marginal increase in myocardial reserve due to |

TABLE II-continued

| Name | Variable | Equation | Description |
|---|---|---|---|
| Myocardial Reserve Index | $M_yRI$ | d(MWI)/d(LVEDP) | a marginal increase in LVEDP Myocardial Reserve normalized by Body Surface Area |
| Stroke Work | SW | $SV * (\overline{(AOP)_{Systole}} - \overline{LVP}_{Diastole})$ | Hemodynamic work performed by the left ventricle during a single cycle |
| Stroke Work Index | SWI | SW/BSA | Stroke Work normalized by Body Surface Area |
| Stroke Work Reserve | SWR | d(SW)/d(LVEDP) | Marginal increase in Stroke Work due to a marginal increase in LVEDP |
| Stroke Work Reserve Index | SWRI | SWR/BSA | Stroke Work Reserve normalized by Body Surface Area |
| Systolic Ejection Period | SEP | Direct measurement | Time during which blood is ejected from LV into Aorta |
| Stroke Power | SP | SW/SEP | Power performed by heart against circulatory system |
| Stroke Power Index | SPI | SP/BSA | Stroke Power normalized by Body Surface Area |
| Stroke Power Reserve | SPR | d(SP)/d(LVEDP) | Marginal increase Stroke Power due to a marginal increase in LVEDP |
| Stroke Power Reserve Index | SPRI | SPR/BSA | Stroke Power Reserve normalized by body surface areas |
| Myocardial Power | MyP | MyW/SEP | Power performed by the myocardia during systole |
| Myocardial Power Index | MyPI | MyP/BSA | Myocardial Power normalized by body surface area |
| Myocardial Power Reserve | MyPR | d(MyP)/d(LVEDP) | Marginal increase in myocardial power due to a marginal increase in end diastolic pressure |
| Myocardial Power Reserve Index | MyPRI | MyPR/BSA | Myocardial Power reserve normalized by body surface area |
| Myocardial Power Requirement | MyPSV | MyP/SV | Power required to deliver unit stroke volume |
| Ejection contractility | EC | $\dfrac{P_2V_2 - P_1V_1}{(t_2 - t_1)\int_{t_1}^{t_2} Q\,dt}$ | Instantaneous power over instantaneous stroke volume (units: dP/dt) |
| Cardiac Efficiency | CE | $SW/M_yW$ | Efficiency of the heart in converting myocardial work into circulatory work |
| Cardiac Amplification | CA | d(SV)/d(LVEDV) | Marginal increase in stroke volume due to a marginal increase in LVEDV |
| Valvular Gradient | VG | $\Delta P_{max}$ | Maximum (during a cycle) pressure gradient across a valve |
| Valvular Gradient Reserve | VGR | d(VG)/d(LVEDP) | Increase in VG as a function of increase in LVEDP. |
| Valvular Area | VA | $0.11 * SV\sqrt{\Delta P}$ | Standard calculation of valvular area using mean pressure gradient and mean flow rate |
| Valvular Area Reserve | VAR | d(VA)/d(LVEDP) | Increase in valvular area as a function of increase in LVEDP |
| Valvular Regurgitation | VR | $\int Q_{REGURGITATION}$ | Cumulative regurgitant flow during a cycle |
| Valvular Regurgitation | VRR | d(VR)/d(LVEDP) | Increase in regurgitant |

TABLE II-continued

| Name | Variable | Equation | Description |
|---|---|---|---|
| Reserve | | | flow as a function of increase in LVEDP |

Some of the methods for measuring and calculating cardiac parameters according to principles of the present invention are described below. These methods are not an exhaustive list of the methods which may be employed according to the present invention as described in the appended claims.

Exemplary Methods for Determining Left Ventricular End-Diastolic Pressure (LVEDP), Left Ventricular End-Systolic Pressure (LVESP), and Aortic Pressure (AOP)

In one embodiment, catheter 102 may be used in a left heart catheterization procedure, and thus measure cardiac parameters relating to the left ventricle. Other embodiments, however, may be optimized for other chambers of the heart and, thus, may measure parameters in one or more of the other three chambers of the heart. Thus, LVEDP and EDP (End Diastolic Pressure) may be occasionally used interchangeably in this application, as LVEDP is merely one example of EDP.

In one embodiment, LVP (Left Ventricular Pressure) may be measured using a microfabricated pressure sensor attached to the catheter and introduced into the left ventricle. In alternate embodiments, an external pressure sensor is hydraulically linked by a lumen in the catheter to the body fluids of the left ventricle. Similarly, AOP is measured in some embodiments using a second microfabricated pressure sensor attached to the catheter. In alternate embodiments, AOP may be measured with the first microfabricated sensor or an external pressure sensor hydraulically linked to the aorta.

One method of determining LVEDP is to record left ventricular pressure (LVP) at point in time when left ventricular volume (LVV) is at a maximum, that is, just as the ventricle is about to contract. An alternate method comprises recording LVP at the "R" point of the Q-R-S cycle of an electrocardiogram (ECG). Another alternative comprises monitoring the left ventricular pressure continuously and using a pattern recognition algorithm to find the pressure when change in pressure divided by change in time equals zero (dP/dt=0) and $d^2P/de$ is>0 just before dP/dt becomes maximum. Still another alternative method for determining LVEDP is to measure the pressure when the "first" heart sound "S1" stops, which occurs when the mitral valve is closed. To obtain the heart sounds, a pressure sensor may be used to sample the pressure signal at about 2000 times per second (or any other suitable frequency) and filter out the lower frequency components associated with increase in blood pressure. Alternatively, the catheter may employ a dedicated hydrophone for monitoring acoustic signals emanating from the valves or defects such as shunts.

One method of determining LVESP is to record LVP when LVV is at a minimum, which is the point of minimum left ventricular volume. Another method of determining LVESP is to record LVP when the blood velocity in the aorta first becomes zero after reaching a maximum positive number, which is the point at which blood first stops flowing into the aorta. A significant difference between these two values might indicate and allow quantification of mitral regurgitant flow (or flow through shunts to the right side) after the aortic valve closes. An alternative method would be to record LVP when the "T" wave on the ECG has just ended. The pressures measured these three ways should give nearly identical results; therefore a comparison of any differences might help indicate a physiological abnormality.

Method for Determining Left Ventricular End-Diastolic Volume

One currently used method for determining LVEDV employs one or more x-ray images of the heart and a manual drawing of the ventricular perimeter using an electronic cursor. These outlines are then used in conjunction with an empirical estimating formula to calculate an estimate of the heart's volume at end diastole. This technique is cumbersome and time consuming, making it impractical for estimating numerous end-diastolic volumes. In addition, since only one or two projections of the heart are used, a significant error is implied in the measurement.

Another currently available technique uses an external ultrasound transducer to image the whole heart and also measure volume. This is a fairly accurate technique, but since the ultrasound transducer is outside the body, it is incapable of simultaneously measuring pressure or changing end diastolic pressure. In addition, not all patients have anatomy which is amenable to an ultrasonic imaging system. Nevertheless, this approach could be used in conjunction (simultaneously) with a catheter that doesn't feature the volume-measuring capability.

In one embodiment of the present invention, a method of measuring volumes in body cavities such as a heart chamber, involves using six ultrasound transducers mounted orthogonally to each other, as shown in FIG. 10. Two of the transducers are mounted parallel to the catheter and thus measure a distance perpendicular to the axis of the catheter. The other four transducers are mounted in pairs on surfaces that are axially 90 degrees rotated from the first pair of sensors but also tilted 45 degrees up or down. Thus, the latter four transducers measure the distance between them and the wall of a heart chamber in four directions which are all orthogonal to each other. Another way of describing the arrangement is that of six transducers each mounted on a face of a cube. The cube is then rotated 45 degrees about one of the faces and mounted-over a catheter body. To facilitate manufacturing of the catheter while keeping a slim profile, the cube may be "disassembled," i.e., the transducer pairs are not necessarily contiguous. The transducer assembly might also be part of an inflatable or expandable assembly to project into the ventricle somewhat during measurement.

An alternative method for measuring ventricular volumes is to use a phased array ultrasonic imaging system with circular electrodes, i.e. rings about the catheter. These rings may be excited slightly out of phase with each other to send the wave up or down relative to the perpendicular of the catheter. The signals returning to the rings would be distributed over time, depending upon the distance from the catheter to the ventricular wall in the various segments of the ring. Thus, the amplitude over time of the reflected signal would correspond to the various radial distances between the catheter and the wall of the heart chamber. Making numerous measurements at various angles from normal in a very short period, the system makes multiple cross-sectional area measurements of the ventricle that are then added using Taylor's method for estimating volumes (similar to what is done using external ultrasonic arrays). Yet a third method of measuring ventricular volumes would be to use two pairs of planar phased array sensors, each parallel pair perpendicular to the other, so that four sides of a catheter are mounted with a phased array transducer. Each of the sensors may, as above, measure a distance to the wall in order to measure, at any given angle from the transducers, four radii to the ventricular wall. Taylor's method is then used as before to estimate true ventricular volume.

One method of estimating LVEDV is to record LVV, measured using one of the above methods, at the point of time when it is at a maximum. In an alternative method, an array of electrical conductance sensors on the catheter is used to determine the average conductance of the ventricular blood. A volume of liquid with a known and different electrical conductivity is dispersed into the left ventricle during diastole. At end diastole and during systole, the conductivity in the ventricle is monitored. These measurements produce an estimate of the diluted electrical conductance of the ventricular blood. Then, knowing the volume of injected blood ($V_I$), the electrical conductance of the injected blood ($k_I$), the conductance of the undiluted blood ($k_B$), and the conductance of the diluted blood ($k_D$), one may compute the end diastolic volume using the following equation:

$$V_D = V_I \frac{k_I - k_B}{k_D - k_B}$$

Another method of estimating end diastolic volume uses an array of temperature sensors on the catheter to determine the temperature of the blood. A quantity of blood at a lower temperature is injected into the ventricle during diastole. The temperature of the diluent may be measured just before it leaves the catheter, to improve accuracy. Then, knowing the volume of injected blood ($V_I$), the specific heat of the blood ($C_B$), the specific heat of the diluent ($C_I$), the undiluted temperature of blood ($T_B$), the temperature of the diluent ($T_I$), and the average temperature of the diluted blood at end diastole ($T_D$), the end diastolic volume ($V_D$) is given by the following equation:

$$V_D = V_I \left(1 + \frac{C_I(T_D - T_I)}{C_B(T_B - T_D)}\right)$$

In another embodiment, a method of estimating end diastolic volume uses an array of light sources and optical sensors, perhaps incorporating optical fibers. A volume of a solution containing a dye of a known concentration is injected and dispersed into the ventricle during diastole. The concentration of dye in the blood may be measured using either absorption or fluorescent techniques. A fluorescent technique, for example, would entail shining light of one wavelength into the blood and detecting the intensity of light at a different (fluorescent) wavelength. The concentration of dye in the blood would be a linear function of the ratio of the intensity of the fluorescent light over the intensity of the exciting light. Then, knowing the volume of injected blood ($V_I$), the concentration of dye in the undiluted blood ($D_B$), the concentration of dye in the diluent ($D_I$), and the average concentration of dye in the diluted blood at end diastole ($D_D$), the end diastolic volume ($V_D$) is given by the following equation:

$$V_D = V_I \frac{D_B - D_I}{D_B - D_D}$$

In other embodiments, it may be useful to determine an end-diastolic volume without introducing fluid to the ventricle. In some embodiments, it may even be useful to reduce the end-diastolic volume or end-diastolic pressure from the resting value. To accomplish this, a catheter may include a balloon that can hold at least as much volume as the diluent (either thermal, conductive, or dye diluent or none if ultrasound is used to measure volume, as in the preferred method). The balloon is first inflated in the ventricle during the systolic phase of the previous cycle, helping to eject a corresponding amount of blood from the ventricle. To determine the end-diastolic volume without influencing it, the balloon is simultaneously and completely deflated during diastole by a volume equal to the volume of diluent injected into the ventricle at the same time. Thus, as the balloon shrinks, the diluent is added to the ventricle without increasing or decreasing the pressure in the ventricle. It may be useful to decrease the end-diastolic volume and/or end-diastolic pressure from an at-rest state while determining the end-diastolic volume. This may be accomplished by first inflating the balloon during the systolic phase or, in the case of repeated cycles, just after the aortic valve has closed. Then, during diastolic filling of the ventricle, an amount of diluent is dispersed into the ventricle. The balloon is simultaneously and completely deflated by a volume greater than the volume of diluent added, reducing the end diastolic pressure and volume. The end-diastolic volume is determined using one of the dilution methods described above. In one embodiment, one or more ultrasound transducers are used to measure the ventricular volume continuously while the balloon is inflated during systole and deflated in diastole to reduce the end-diastolic pressures and/or volumes.

Methods for Determining End-Systolic Volume

One method for measuring LVESV is to record LVV when it is at a minimum, using one of the continuous volume measuring systems. An alternative method for measuring for LVESV is that LVV when aortic flow rate is first zero following its maximum. The difference in volumes of these two recordings is equal to the combination of mitral regurgitant flow and left-to-right shunt flow after the aortic valve is closed.

Methods for Determining Ejection Fraction

Ejection Fraction is typically defined as the ratio of the difference between end-diastolic volume and end-systolic volume over end-diastolic volume. This calculation may be made, using any of the above-described methods of measuring EDV and ESV.

Methods for Determining Cardiac Output, Cardiac Index, Stroke Volume, and Stroke Volume Index on a Per-Stroke Basis In one embodiment, a blood velocity or flow rate sensor is coupled with the catheter and inserted into the aorta. This sensor samples the velocity of blood at regular intervals, such as approximately once every millisecond, and transmits that information to a controller or other processor. The controller then determines the average blood velocity by averaging the readings taken over a second (or some other similar period of time that is representative of the next step).

During that sampling time, the cardiac output is independently measured using one of the accepted methods, such as Fick's Law using oxygen consumption or a dilution method (thermal dilution, conductance dilution or dilution with a dye). (Grossman's *Cardiac Catheterization and Anziography*, pp. 101–117 describes these methods in detail). The cardiac output thus measured is divided by the average velocity or flow rate to determine a scaling coefficient. This coefficient assumes that the aortic cross section near the velocity or flow rate sensor is reasonably constant during the sampled cycle and successive cycles. A number of different methods of measuring blood velocity or flow rate are possible, including thermal dilution, shear force measurement, a pitot-tube method (stagnant versus dynamic flow), Ultrasound Doppler, and/or any other suitable method. Once the scaling factor has been determined, the stroke volume may be determined for any given cycle and is equal to the product of the scaling factor and the integral of velocity through that cycle. The stroke time is also calculated as that period between successive end-diastolic events. Cardiac output is then calculated as the ratio between stroke volume over stroke time, adjusted to correct units. Cardiac index is cardiac output divided by body surface area (BSA), which is a known value based on a patient's height and weight. Stroke volume index is stroke volume divided by BSA.

Methods for Determining Cardiac Reserve and Cardiac Reserve Index

In one embodiment, a method for measuring cardiac reserve involves first measuring LVEDP at the beginning of one cardiac cycle and then measuring the cardiac output during that cycle using the methods described above. This measurement may be repeated any number of times and multiple data pairs (LVEDP, CO) may be taken. Then, an amount of fluid is injected into the left ventricle during a diastole period and the resulting end-diastolic pressure recorded. The cardiac output for that cycle is recorded using the methods described above and a new data point (LVEDP, CO) is recorded. This process is repeated as desired to create a set (n>=2) of data pairs. A line of regression is then fit through the data points using a least-squares technique. The slope of that line is equal to cardiac reserve. Cardiac reserve index is equal to cardiac reserve divided by BSA.

Methods for Determining Stroke Reserve and Stroke Reserve Index

One method of measuring cardiac reserve is to first measure the LVEDP and the beginning of one cardiac cycle and then measuring stroke volume during that cycle using the methods described above. This measurement may be repeated any number of times and multiple data pairs (LVEDP, SV) taken. Then, an amount of fluid is injected into the left ventricle during a diastole period and the resulting end-diastolic pressure recorded. The stroke volume for that cycle is recorded using the methods described above and a new data point (LVEDP, SV) is recorded. This process is repeated as desired to create a set (n>=2) of data pairs. A line of regression is then fit through the data points using a least-squares technique. The slope of that line is equal to stroke reserve (SR). Stroke reserve index (SRI) is equal to SR divided by BSA.

Methods for Determining Myocardial Work Myocardial Work Index, Myocardial Work Reserve, and Myocardial Work Reserve Index Myocardial work ($M_YW$) comprises the work performed by the myocardium against the blood in the heart during a single heart cycle. It is mathematically defined as the integral of Pressure and dV as V varies from V(max) to V(min) minus the integral of Pressure and dV as V varies from V(min) to V(max). Thus it is the work performed by the heart tissue during systole minus the work performed on the heart tissue by the body during diastole. Myocardial work may thus be expressed as the difference between the integral of the pressure and volume while the volume is decreasing from the integral of the pressure and volume while the volume is increasing:

$$SW = \int_{dV/dt<0} Pdv - \int_{dV/dt>0} Pdv$$

Myocardial work index (MWI) is equal to the myocardial work divided by BSA.

In some embodiments, it may also be advantageous to calculate the first moment of work, which could also be useful for optimization. The first moment of work is calculated as:

$$SW = \int_{dV/dt<0} PVdv - \int_{dV/dt>0} PVdv$$

In one embodiment, myocardial work reserve is calculated by first recording the LVEDP of a given heart cycle and then calculating the myocardial work during that cycle. This measurement may be repeated any number of times and multiple data pairs (LVEDP, $M_YW$) taken. Then, an amount of fluid is injected into the left ventricle during a diastole period and the resulting end-diastolic pressure recorded. The myocardial work for that cycle is recorded using the methods described above and a new data point (LVEDP, $M_YW$) is recorded. This process is repeated as desired to create a set (n>=2) of data pairs. A line of regression is then fit through the data points using a least-squares technique. The slope of that line is equal to Myocardial reserve ($M_YR$). Myocardial reserve index (MRI) is equal to myocardial reserve divided by BSA.

Methods for Determining Stroke Work, Stroke Work Index, Stroke Work Reserve, Stroke Work Reserve Index, and Cardiac Efficiency Stroke work (SW) is typically defined the work performed by the left ventricle on the circulatory system. This relationship is displayed in graphic form in FIGS. 4A and 4B. In one embodiment of the present invention, stroke work is determined by calculating the integral of the product of volume ejected into the aorta and pressure increased by the ventricle. In some embodiments, the average filling pressure is determined and subtracted from the ventricular pressure during systole. This difference is then multiplied by the quantity of blood flowing into the aorta. This product is then integrated over a single stroke to calculate stroke work.

$$SW = \int_{cycle} V_{Aorta}(P_{systole} - \overline{P_{diastole}})$$

Thus, SW is distinguishable from myocardial work. The difference between these two parameters involves a difference in how regurgitant flow plays into the measurements. Myocardial work measures the work that the heart muscle performs, while SW measures the work the heart performs against the circulatory system. Cardiac efficiency (CE), yet another parameter which may be measured according to the present invention, is defined as the ratio of SW over myocardial work and is a measure of the efficiency with which the heart converts myocardial work into stroke work. This parameter may be used, for example, by biventricular pacing devices to optimize their performance.

In an alternative embodiment, stroke work may be calculated by taking the integral of the product of aortic pressure and aortic flow rate minus the integral of the product of left atrial pressure and flow through the mitral valve. With either of the two methods described above, the stroke work index is equal to stroke work divided by BSA. A similar set of calculations is possible for the right ventricle, where stroke work would be the integral of the product of the pressure in the Pulmonary Artery times the systolic volume flowing into the Pulmonary Artery minus the integral of the right atrial pressure times the diastolic volume flowing into the right ventricle.

In some embodiments, stroke work reserve is calculated by first recording the LVEDP of a given heart cycle and then calculating the stroke work during that cycle. This measurement may be repeated any number of times and multiple data pairs (LVEDP, SW) taken. Then, a predetermined amount of fluid is injected into the left ventricle during a diastole period and the resulting end-diastolic pressure recorded. The stroke work for that cycle is recorded using the methods described above and a new data point (LVEDP, SW) is recorded. This process is repeated as desired to create a set (n>=2) of data pairs. A line of regression is then fit through the data points using a least-squares technique. The slope of that line is equal to stroke work reserve (SWR). Stroke work reserve index (SWRI) is equal to SWR divided by BSA.

Methods for Determining Cardiac Amplification

Cardiac amplification (CA) may be defined as the marginal increase in stroke volume due to a marginal increase in end-diastolic volume. In one embodiment, cardiac amplification is calculated by first recording the LVEDV of a given heart cycle and then calculating the stroke volume during that cycle. This measurement may be repeated any number of times and multiple data pairs (LVEDV, SV) taken. Then, an amount of fluid is injected into the left ventricle during diastole and the resulting end-diastolic volume is measured. The stroke volume for that cycle is measured using the methods described above and a new data point (LVEDV, SV) is recorded. This process is repeated as desired to create a set (n>=2) of data pairs. A line of regression is then fit through the data points using a least-squares technique. The slope of that line is equal to cardiac amplification.

Methods for Determining Valvular Gradient, Valvular Gradient Reserve, Valvular Area, Valvular Area Reserve, Valvular Regurgitation, and Valvular Regurgitation Reserve In one embodiment, valvular pressure gradient (VG) may be measured directly using two pressure sensors one upstream and the other downstream of a heart valve, as in the aortic valvular pressure gradient. In another embodiment, VG may be measured somewhat indirectly, as in the case of the mitral valve, where upstream pressure may be measured using a known pulmonary capillary wedge pressure measurement technique and downstream pressure is measured in the left ventricle. In either case, a pressure gradient across a valve may be measured throughout the appropriate filling period while the flow through the valve is simultaneously determined. In the case of an aortic valve, the flow through the valve is measured using the aforementioned scaled velocity sensor in the aorta; in the case of the mitral valve, the flow is measured as the diastolic change in ventricular volume minus any regurgitant aortic flow measured by the scaled velocity sensor in the aorta. Throughout the filling period, multiple data pairs are recorded in the form of ($\Delta P$, Q), where $\Delta P$ is the pressure gradient and Q is the instantaneous volumetric flow rate through the valve. The maximum pressure gradient ($\Delta P$) during any cycle may then be recorded as the VG for that cycle.

The total regurgitant flow through the valve in a cycle—valvular regurgitation (VR) may be calculated as the integral of the reverse volumetric flow rate during a cycle. In the case of aortic, pulmonic or tricuspid regurgitation, this flow may be directly determined using the output of the scaled velocity sensor, and is the scaled integral of all negative volumetric flow rates during a cycle. In the case of the mitral valve, regurgitant flow may be determined by subtracting the stroke volume (measured in the aorta using the scaled velocity sensor) from the difference between the maximum and minimum left ventricular volumes (LVEDV–LVESV). Thus mitral regurgitant flow, in the absence of shunts, is equal to LVEDV–LVESV–SV. In some embodiments, measurement of mitral regurgitation may include factoring in any aortic regurgitation that is present. Since calculating stroke volume includes subtracting regurgitant (diastolic) aortic flow from the total amount of blood ejected into the aorta during a given cycle, in some embodiments the amount of aortic regurgitation is added back in to give a more accurate measurement of mitral regurgitation. Therefore, MR=LVEDV–LVESV–SV+AR, where MR is the net systolic mitral regurgitant flow, and AR is the net (diastolic) aortic regurgitant flow.

To calculate the effective area of a valve, one embodiment uses a known formula (the Gorlin Formula—see Grossman's *Cardiac Catheterization and Angiography*, p143). Using the known formula, average flow rates such as cardiac output and mean pressure gradients are used to calculate a mean orifice area. So, this embodiment uses these mean values to calculate the effective valvular area. The equation for mean mitral valve area $$(MMVA) \text{ is } \frac{CO/(HR*DFP)}{(44.3*0.85)\sqrt{\Delta P}},$$

where CO is Cardiac Output in cc/min, HR is beats/min, DFP is filling period in seconds/beat, and $\Delta P$ is the mean pressure gradient across the mitral valve in mm Hg. This technology enables the real time estimate of valvular area by using instantaneous measures of flow rate and pressure gradient. Thus mitral valve area (MVA) is $$\frac{Q}{(44.3*0.85)\sqrt{\Delta P}},$$

where Q is the volumetric flow rate through the valve at any point in time and $\Delta P$ is the pressure gradient at approximately the same point in time. (This pressure gradient is typically measured with the assistance of a right heart catheter and is the difference between the pulmonary capillary wedge pressure from the left ventricular pressure). With this equation—modified from Gorlin and Gorlin's original—it is possible to measure orifice diameter as a function of time.

A similar equation is found for the aortic valve: mean aortic valve area (MAVA) is $$\frac{CO/(HR*SEP)}{(44.3)\sqrt{\Delta P}},$$

where SEP is the Systolic Ejection Period and ΔP is this time the pressure gradient across the aortic valve. Similarly, a real time measurement of aortic valve area (AVA) is $$\frac{Q}{(44.3)\sqrt{\Delta P}},$$

where Q is the instantaneous volumetric flow rate through the aortic valve, as measured using the scaled velocity sensor in the aorta and ΔP is the pressure gradient across the aortic valve.

In one embodiment, variations in the above-described parameters (regurgitant flow, valvular area, and pressure gradient) with increasing cardiac output, are measured. One method for measuring such variations comprises first measuring LVEDP for a given heart cycle. At the completion of that cycle, additional parameters related to a valve are measured—for example, valvular regurgitation(VR), valvular area (VA), and valvular pressure gradient (VG). Any number of these cycles may be recorded, so that multiple measurements may be averaged together. On a successive cardiac cycle, an amount of fluid is introduced into the left ventricle during diastole to increase end-diastolic pressure and the resultant values are again measured, typically (but not always) with a higher cardiac output (resulting from the higher LVEDP). Multiple data sets are thus generated. To obtain the valvular gradient reserve (VGR), a least squares method is used to fit a line is fit between the multiple data pairs (LVEDP, VG). The slope of that curve is VGR. As cardiac output doubles, the pressure gradient should quadruple, so VGR would be expected to increase with increasing cardiac output. It nevertheless represents the marginal increase in gradient with increasing LVEDP within the corresponding range of LVEDP.

In various embodiments, valvular area reserve (VAR) may be obtained by using a least squares method to fit a line between the various data pairs (LVEDP, VA). The slope of that fit line is VAR, which represents the marginal increase in valvular area due to a marginal increase in LVEDP. There are some patient populations (some disease states) where the effective area decreases with increasing cardiac output, and this value would be negative for that class of patient.

Similarly, valvular regurgitation reserve (VRR) may be obtained by using a least squares method to fit a line between the various data pairs (LVEDP, VR). The slope of this line is VRR, which represents the marginal increase in valvular regurgitation due to a marginal increase in LVEDP. Any of these "reserve" measurements could be made relative to cardiac output (or LVEDV, or any other variable), instead of LVEDP.

Methods for Generating Frank-Starling Curves

A Frank-Starling (F-S) curve has many definitions in the literature. They all generally relate to the change in hemodynamic output of the left ventricle due to changes in the left ventricular end-diastolic volume (LVEDV) or left ventricular end-diastolic pressure (LVEDP). The most common types of F-S curves are: Cardiac Output v. LVEDP, Cardiac Output v. LVEDV, Stroke Work v. LVEDP, Stroke Work v. LVEDV, and LVESP/LVEDP v. LVEDV.

In some embodiments, an F-S curve places Cardiac Output (CO) on a vertical axis and LVEDP on a horizontal axis. The catheter system records the LVEDP at the beginning of one or more heart cycles and then calculates the CO at the end of each corresponding cycle. By introducing and/or removing fluid (or increasing or reducing the volume of an inflatable balloon), the system adjusts the end-diastolic pressure to a new value and measures that value. It then calculates the resulting cardiac output for that cycle. By repeating this process over several cardiac cycles, each using a different LVEDP as it's starting point, a graph of CO v. LVEDP is generated, recorded, and displayed to be seen by the physician.

In other embodiments, an F-S curve that represents Cardiac Output v. LVEDV may be generated. Any of the above-described methods may be used for measuring CO on a per stroke basis and LVEDV on a per stroke basis. Then, by introducing and/or withdrawing amounts of fluid from the ventricle during diastole, one may vary the LVEDV for one or more cycles of the heart. If a reduced starting volume of the heart is desired, for example to simulate a reduction in preload, a balloon may be attached to the catheter and inflated during the systolic phase of the previous heart cycle. The balloon is then deflated during diastole to simulate a reduction in preload.

Another variation of an F-S curve is to have either myocardial work (MyW) or stroke work (SW), both defined above, on the vertical axis and LVEDP on the horizontal axis. The difference between the two measures is an important indicator of valvular disease related to the left ventricle. In a manner similar to that described above for CO v. LVEDP, the system may be used simultaneously calculate MyW and SW for each LVEDP. Cardiac efficiency (CE), the ratio of SW over MyW, may also be calculated and displayed, showing how the efficiency of the heart changes at increasing levels of LVEDP and perhaps correspondingly increasing levels of cardiac output. Any of the above-described parameters may be plotted against any other suitable parameter or parameters, as desired.

In one embodiment, to generate a CO v LVEDP curve, a real-time cardiac output sensor is coupled with the catheter so that it resides in the aorta. This real time sensor may be calibrated using one or more of several accepted methods of measuring cardiac output, such as Fick's method based on oxygen consumption or the dilution method. The CO sensor may be used to measure the volume of blood ejected from the left ventricle during each cycle. At the same time, another sensor on the catheter measures pressure inside the left ventricle. During diastole, the catheter system introduces saline or other fluid into the left ventricle and measures the resulting LVEDP. Then, as the heart completes its cycle, the CO sensor measures the output of the heart during that cycle. The result represents a single point on the CO v LVEDP curve. After some period of time, a second point is plotted on the curve by injecting a second bolus of saline or other liquid into the left ventricle during diastole. The cardiac output and LVEDP are then measured for that cycle and the second point is plotted. Additional points are generated during successive cycles and as various LVEDP conditions are created, as desired.

In another embodiment, an F-S curve based on a different definition of stroke work is generated using a method similar to the one just described. Stroke work is calculated simultaneously (or nearly simultaneously) with cardiac output (i.e. during the same cycle). One definition of stroke work which may be used is the integral of the product of pressure and stroke volume during a single cycle. Another definition uses the change in volume of the ventricle to determine the work performed by the heart. This latter measurement, however, includes work required to pump regurgitant flow retrograde against the mitral valve as well as work lost to regurgitant aortic flow. In an additional embodiment, the stroke work is the product of the volume of blood ejected into the aorta multiplied by the pressure gradient between the ventricle and the aorta. The volume of blood ejected into the aorta is measured by the blood velocity sensor and the pressure gradient is measured using the difference between two pressure sensor, one in the ventricle and the other in the aorta near the velocity sensor.

As previously discussed, catheters in many embodiments of the present invention include means for effecting end-diastolic pressure and/or volume by introducing and/or withdrawing an amount of fluid (such as saline, glucose, or any other suitable fluid) into or from the ventricle at a desired time during a heart cycle, such as during diastole. In one embodiment, fluid introduction is achieved by driving an external actuator, such as a pump, coupled with the catheter using control signals from the controller, such as a computer or other data processor. The timing of fluid introduction and/or withdrawal may be based upon measurements taken via a pressure sensor in the heart chamber. Such measurements may be taken at any suitable interval, but in some embodiments they are taken at a rate of about 1000 Hz.

Methods for Generating Pressure/Volume Loops

With reference now to FIGS. 4–9, information which may be generated and optionally displayed according to one embodiment of the invention is shown. This information is generally referred to as "pressure-volume loops," and such information may be displayed in various forms. In one embodiment, a catheter is used to generate pressure-volume loops by measuring on a simultaneous or near-simultaneous basis intracavitary pressure and volume. The volume may be measured, for example, using six orthogonally oriented ultrasound transducers, as described in detail above. Referring to FIGS. 10 and 11, one embodiment of such a six-transducer device 162 on a catheter 102 is shown. As designated by the arrows in FIG. 11, the six transducers may be used to measure six distances from the transducer device 162 to various locations on the inner wall of the heart chamber. These six distances represent radii of curvature to an inscribed ovoid. One or more phased array transducers may alternatively be used to measure volume. In one embodiment, multiple phased array transducers have at least two arranged axially about the axis of the catheter. In another embodiment, four phased array sensors are arranged axially around the catheter.

Pressure may be measured using readings from one or more pressure sensors located inside the cavity (i.e., the left ventricle in FIG. 11, but any other suitable heart chamber or other cavity is contemplated). In some embodiments, the pressure sensor used in the heart chamber comprises an absolute pressure sensor, so that a pressure sensor sampling the ambient pressure is often used as well, to enable the calculation of a gauge pressure with which most physicians are familiar. This gauge intracavitary pressure comprises the absolute intracavitary pressure minus the absolute ambient pressure. In various embodiments, an ambient absolute pressure sensor may be coupled with the catheter outside of the body or, alternatively or additionally, may be coupled with a controller, a console, and/or the like.

Referring now to FIGS. 5A and 5B, one method of the present invention involves introducing fluid (or inflating an expandable balloon) inside a heart chamber such as the left ventricle during diastole to cause a shift in a pressure/volume loop. The original loop is shown as the points a, b, and c, while the shifted loop (up and to the right) is shown as points a', b', and c'. Generally, introducing a fluid into the left ventricle during diastole may result in a different end-diastolic pressure and/or volume, which may be measured and shown graphically as a shifted pressure/volume curve.

By introducing and/or withdrawing fluid into/from the ventricle during diastole, various end-diastolic pressure and volume conditions for the ventricle are created. The resulting pressure and volume of the ventricle may then be measured continuously as the heart completes its cycle. The integral of pressure multiplied by volume (as measured during one heart cycle) is equal to the stroke work, as shown by the area inside the curve in FIG. 5A and on the vertical axis in FIG. 5B. Stroke work as a function of end diastolic pressure is one measure of ventricular performance. Pressure/volume loops, as in FIGS. 4A and 5A, may be used to generate Frank-Starling curves, which may include any of a number of various parameters, as described in detail above. This is a vast improvement over conventional methods for generating Frank-Starling curves, which involve measurements taken over a period of days using a Swan-Ganz catheter to measure cardiac output, as well as administration of one or more medications to vary the LVEDP.

Referring again to FIGS. 5A and 5B, in some embodiments of the invention, methods may be used to calculate myocardial stiffness and/or compliance of the heart chamber in which a catheter is positioned. In one embodiment, a method of calculating myocardial stiffness involves first measuring pressure and volume when volume is at a maximum (i.e., at end of diastole) and then again when volume is at a minimum (i.e., end of systole). During a subsequent heart cycle, end-diastolic pressure and volume are increased (or decreased) using one or more actuator on the catheter, and the two sets of data points are recorded again. Any suitable number of such pairs of data points may be measured, and they may then be used to generate a pressure/volume curve. A least squares routine may then be used for each set of data pairs (i.e., the end-diastolic set and the end-systolic set) to fit a straight line between each set of points. The slope of the line through the end-diastolic points is the lusitropic stiffness of the heart, and the inverse of that slope is the lusitropic compliance. The slope of the line through the end systolic points is the inotropic stiffness and the inverse of that slope is the inotropic compliance. These measurements and equations used for calculations are shown as labels on FIG. 5A.

In another embodiment, a method of measuring the compliance of a heart chamber involves continuously varying the volume in the chamber and simultaneously measuring pressure in the chamber to give a continuous measure of chamber wall stiffness. In this method, a hydrophone may be used to vary the volume inside the ventricle at any suitable frequency, such as approximately 200 times per second. A pressure sensor is used to measure pressure change at approximately the same frequency at which it is being effected by the hydrophone. By filtering the pressure signal at 200 Hz, one obtains a signal whose amplitude is proportional to the stiffness of the heart throughout the cycle. The inverse of this number is the compliance of the heart throughout the cycle. When either valve to the ventricle is open, the method measures the effective stiffness and compliance of the hydraulically linked chamber. Thus, when the mitral valve is open, the stiffness and compliance of both the left atria and the left ventricle, as well as some of the pulmonary vein, may be measured. When the mitral valve is closed and the aortic valve is open, the combined stiffness of the left ventricle and the aorta may be measured. When both valves are closed, as in isovolumic contraction or isovolumic relaxation, then the stiffness of the left ventricle alone may be measured. Since the pressure/volume slope is rather steep during either isovolumic phase, it may be desired to use a higher frequency such as 1000 Hz or even 5000 Hz to measure stiffness and compliance and how those values change during contraction or relaxation.

FIGS. 6–9 show various ways in which changes in pressure, and thus stiffness, may be displayed over a period of time. FIG. 6 shows a change in pressure when an actuator is used to effect an oscillating volume change. FIG. 7 shows the same change, after being processed through a low-pass filter. FIG. 8 shows the same change, after being processed through a high-pass filter. Finally, FIG. 9 shows the same data as it relates to systolic and diastolic stiffness of the heart chamber.

Methods for Determining Dose/Response Characteristics of Medications

In yet another embodiment, a method of the present invention may be used to measure one or more dose/response characteristics of a medication on various cardiac and/or circulatory functions. Because most patients have somewhat unique responses to a given medication, knowing the dose/response curve of any medication allows for a quantitatively based selection among similar medications, quantitative prediction of optimal dosing levels of the chosen medication, and quantitative comparison of the short term effects of combinations of medications.

In one embodiment of the invention, a method involves administering a nitrate-type medication to a patient in small, increasing doses, while one or more various hemodynamic parameters and performance ratios are monitored. Measured parameters may then be plotted on one axis of a graph, while the dose concentration of the medication is plotted on the opposing axis. For example, Cardiac Reserve (CR) (y-axis) as a function of nitrate dose (x-axis) may be plotted. A three dimensional plot may be used to express, for example, Cardiac Reserve (z-axis) against LVEDP (x-axis) and Nitrate Dose (y-axis), where the x, y, and z axes are isometrically presented as if a corner of a cube.

In a further example, a new "set point," or optimal hemodynamic parameter set for a patient, may be produced by some combination of medications at concentration levels determined during the catheterization. (For example, the LVEDP may be lowered to some value, the cardiac output may be increased to some value, and the SVR may be lowered to some value, each of which is expected to have a therapeutic benefit.) The patient could then be given a "prescription" using similar-acting oral medications to maintain that set point long after the catheterization has ended.

In a further example, the catheter may be placed in the aorta, where the stiffness and compliance of the aorta may be directly measured. This type of measurement might be used before and after a drug treatment (for example, EDTA may be infused into the femoral vein) to test the effectiveness of that medication in increasing aortic compliance. Similarly, the catheter may be placed in the left ventricle and the patient given an inotropic agent whose purpose is to modify the compliance of the ventricle. Without changing the end diastolic pressure, the effect of the medication on ventricular compliance as a function of dosing levels may be directly measured, recorded and displayed.

As previously described, one or more implantable sensors 18 may be used in addition to or in place of catheters 14 in a system of the present invention. In various embodiments, implantable sensors provide measurements which may be used for calculation of a number of cardiac performance parameters, some of which are similar to those described above and others of which are different. Some exemplary parameters which may be calculated from implantable sensor measurements are set forth in Table III below.

TABLE III

| Calculated Cardiac Performance Value | Algorithm |
|---|---|
| Cardiac Output (CO) | $\dfrac{Q(O2_{inhaled} - O2_{exhaled})}{(O2_{left\ ventricle} - O2_{right\ ventricle})}$ |
| Stroke Volume (SV) | CO/BP |
| Left Ventricular Pressure (LVP) | $P_{left\ ventricle} - P_{ambient}$ |
| Right Ventricular Pressure (RVP) | $P_{right\ ventricle} - P_{ambient}$ |
| Ventricular Performance Value (I) (ischemia) | $\left(\dfrac{P_{maximum\ ventricular} - P_{minimum\ ventricular}}{F_{myocardial\ maximum} - F_{myocardial\ minimum}}\right)$ |
| Hypertrophy Value (H) | $\dfrac{SV}{(D_{myocardial\ maximum} - D_{myocardial\ minimum})^3}$ |
| Cardiac Myopathy Value (M) | $\dfrac{SV(P_{left\ ventricular\ maximum} - P_{right\ ventricular\ minimum})}{(F_{myocardial\ maximum} - F_{myocardial\ minimum})(D_{myocardial\ maximum} - D_{myocardial\ minimum})}$ |
| Cardiac Elasticity Value (E) | $\dfrac{(P_{ventricular\ maximum} - P_{ventricular\ minimum})V_{ventricular\ maximum}}{(SV)(P_{ventricular\ maximum})}$ |
| Myocardial Elasticity (ME) | $\left(\dfrac{F_{mycardial\ maximum} - F_{myocardial\ minimum}}{F_{mycardial\ maximum} + F_{myocardial\ minimum}}\right)\left(\dfrac{D_{mycardial\ maximum} + D_{myocardial\ minimum}}{D_{mycardial\ maximum} - D_{myocardial\ minimim}}\right)$ |

TABLE III-continued

| Calculated Cardiac Performance Value | Algorithm |
|---|---|
| Systemic Resistance ($R_S$) | ($P_{\text{left ventricular maximum}} - P_{\text{right ventricular minimum}}$)/CO |
| Pulmonary Resistance ($R_P$) | ($P_{\text{right ventricular maximum}} - P_{\text{left ventricular minimum}}$)/CO |

A number of the above numbers are dimensionless, allowing comparison of the values among patients, e.g. the hypertrophy value (H) and the elasticity values (E and ME). In other instances, however, the calculated cardiac performance values are not dimensionless, but may be "normalized" so that the values become dimensionless and may be compared among patients. For example, the ventricular performance value (I) may be normalized by multiplying the $\Delta P/\Delta F$ value by the area of the sensors or an area of the patient's heart or ventricle. The cardiac myopathy value (M) may be normalized by a ratio of the area of sensors used to make the measurements ($SA/(SA_{LV}+SA_{RV})$) over a cardiac area of the patient.

Usually, the algorithms set forth above for calculating the various cardiac performance parameters will be programmed into the processor 12. Certain of the cardiac performance parameters, such as cardiac output and stroke volume will be utilized in calculation of a number of the other cardiac performance values. Certain cardiac performance parameters, such as the ventricular performance value and the ventricular elasticity, may be calculated separately for each of the left and right ventricles. Thus, when referring to a ventricular value for the calculation of either of these performance parameters, all values should come from either the right ventricle or the left ventricle, depending on the ventricle for which the value is to be calculated.

The various directly measured cardiac characteristics and calculated cardiac performance parameters may be determined periodically or over extended periods of time. For those values which require measurement of cardiac output or stroke volume, however, if measurements are performed only with implantable sensors, the patient will usually be wearing a mask or other hardware for determining oxygen consumption. The values which do not require measurement of cardiac output or stroke volume, in contrast, could be measured continuously only with implantable sensors, even while the patient is ambulatory. For such ambulatory measurements, the repeater or other circuitry will usually be used to store data, and such collected data will be periodically transferred to the external controller or other evaluation apparatus. By periodically and/or continuously measuring some or all of the physiologic parameters and cardiac performance values, the health of the patient's heart can be followed over time. After establishing a base line, deviations from the baseline will be indicative of either deterioration of heart performance or more hopefully stabilization or even improvement in heart performance. Monitoring deviations from the baseline performance can provide a more quantitative measurement of a patient's response to medications, potentially allowing adjustment in dose levels or changes to different medications as the cardiac performance changes.

In addition to those physiologic parameters and calculated cardiac performance values described above, implantable sensor devices may be utilized to allow measurement and calculation of a variety of other parameters which have conventionally been obtained during cardiac catherization. For example, ventricular pressure may be measured by simply subtracting ambient pressure from the measured ventricular absolute pressure. Left ventricular end diastolic pressure may be determined as the left ventricular pressure measured at the time the ventricle begins to contract, which may be signaled for example, by an EKG or by the pressure signal itself. Alternatively, the pressure may be measured at the point when myocardial thickness is at a minimum, which may be uniquely established with the methods and systems of the present invention.

Left ventricular end systolic pressure may similarly be measured as the left ventricular pressure at the point when the ventricle has just contracted to eject blood. This may be determined based on the EKG, the pressure signal itself, or alternatively, when the myocardial thickness is at a maximum.

Other parameters measured by the system may also find use, such as ventricular stiffness, which can be the ratio of myocardial force over myocardial thickness. An alternate method of determining ventricular stiffness which is more directly correlated to the method in common use today is to first convert a myocardial thickness measurement into a number that represents the volume of the left ventricle. This is done by establishing during implantation a relationship, e.g., a look-up table between myocardial thickness and left ventricular volume. Then, during use, the measured myocardial thickness can be converted into a number that represents ventricular volume. This ventricular volume number may be corrected for subsequent hypertrophy of the left ventricle using the hypertrophy parameter, H, defined above, which quantifies the change in the relationship between cardiac output as measured using Fick's law (oxygen concentration difference) and myocardial thickness change. This corrected estimate of left ventricular volume is then compared with the simultaneously measured left ventricular pressure. By plotting this estimate of ventricular pressure versus ventricular volume, the pressure/volume loop of the heart may be estimated. From this curve, the end-diastolic pressure/volume relationship is plotted for various end-diastolic volumes. The derivative of these plotted points (dP/dV) becomes an estimate of the lusitropic stiffness. The inverse, dV/dP becomes and estimate of the lusitropic compliance. Similarly, plotting these data pairs at end-systole gives yields the inotropic stiffness and compliance. Specifically, the end-systolic dV/dP slope is the inotropic compliance and the end-systolic dP/dV is the inotropic stiffness.

These measures of inotropic compliance and lusitropic compliance may be used to predict and document the response of the patient to inotropic agents, such as digitalis or cardiac glycosides. In addition, since the implant provides measures of cardiac output, left ventricle end diastolic pressure, and stiffness (inverse of compliance) as well as pulse rate, the doctor will be able to monitor the efficacy of a given inotropic treatment regime as a function of dosage and pulse rate for each patient. This could allow for precise dosage levels of substances where too much can cause immediate problems and too low can result in long term deterioration of the heart. For use with pacing devices, the ability to measure the stiffness as a function of pulse rate would describe an optimal pulse rate for a given dosage. This information, coupled with the data from the oxygen sensor in the right ventricle and the pressure in the left ventricle could be used to tailor the pulse frequency to produce a heart with improved compliance. In addition, a biventricular or multiple lead pacing system could vary the timing of the electric pulses to various leads to produce an optimal compliance at a given pulse rate. Thus, at a low pulse rate, the optimal timing might be setting one, producing the best possible stiffness and maximum cardiac myopathy (efficiency) (M) values for that pulse rate, but at a higher pulse rate necessitated by activity as measured by the oxygen sensor in the right ventricle, the timing values might change to a different setting to produce the best possible stiffness and efficiency (M). The pulse rate, within limits selected by the doctor, may be set by the blood oxygen concentration in the right ventricle.

Pulmonary Resistance, $R_P$, is measured with implanted sensors using the cardiac output CO and the pressure readings LVAP and RVAP, which are the absolute pressures of the left and right ventricles, respectively. Most textbooks will define pulmonary impedance—approximated as a resistance—as the maximum pressure drop between the pulmonary artery and the pulmonary vein divided by the cardiac output. This definition implies that all of the cardiac output is passing through the pulmonary system at the highest pressure gradient, which of course is not precise. Nevertheless, this approximation serves as a reasonable proxy for mean pulmonary resistance. Using this approximation, the maximum pulmonary pressure gradient (PPG) is PPG=maximum (RVAP) minus minimum left ventricle pressure (LVAP) Then, Pulmonary Resistance is simply CO/PPG.

Systemic Resistance is similar. The maximum Systemic Pressure Gradient (SPG) is SPG=maximum (LVAP)−minimum (RVAP). The Systemic Resistance ($R_S$) is simply $R_S$=CO/SPG.

Use of implantable sensors to derive various cardiac performance parameters was just described. Prior to that description, the use of catheter devices, such as multiplexed catheters, for deriving cardiac performance parameters was set forth. Again, the use of these two general types of measuring devices together, in any suitable combination, in contemplated within the scope of the present invention. Using one or more catheters and one or more implantable sensors together in one system may provide useful redundancy and increased accuracy and consistency of measurement. On the other hand, some embodiments of the system may use only one or the other of catheter(s) and implantable sensor(s), perhaps to enhance the simplicity of the system. Any combination is therefore contemplated.

Another method of the invention, for example, involves occasional non-pacing to conserve electrical power consumption and battery life. In this method, the heart is not paced every third, every fourth, or once in some other number of heart cycles. Thus, if the heart is not paced every third cycle, the electrical power consumed from electrical stimulation will be reduced by approximately one third. Using the other sense capabilities, the pacing circuitry will determine if the pacing is necessary every beat or if it may be occasionally skipped. For example, the pacer may wait for some period of time to see if the heart will fire on its own, and then fire only if some period has elapsed without firing.

Similarly, the biventricular pacing—or full pacing—may be omitted occasionally in order to pace with a fewer number of electrodes on the other beats. Thus, a high-electrical-power-consumption/high-hemodynamic-performance pattern of electrode firing may be used some of the time and a lower-power/lower-hemodynamic-performance power consumption sequence may be used on the other beats. In this way, the power consumption is reduced and the benefits of optimal timing are delivered on a less-than-every-beat frequency.

Thus, in this context, a general case is that each pacing cycle may use a different pattern of electrodes, including the pattern of "none." For example, a pacer might have the following sets of electrode selection and timing patterns:
1) No pacing
2) Minimal power consumption, single lead pacing
3) Minimal power consumption, biventricular pacing
4) A-V sequential pacing (optimizes atrial output by causing it to contract ahead of the ventricle)
5) Optimal efficiency setting (maximizes stroke work per unit of myocardial work)
6) Optimal Cardiac Output setting (maximizes cardiac output at the cost of lower cardiac efficiency.)

Then, the pacing device may alternate between all of them or any subset. The choice of which sets to use for any given heart cycle may be:
a) Programmed by the doctor and not changed in the field, choosing some combination of the above on either a predetermined schedule or some strict rules-based system (e.g.: after 10 PM and before 7 AM use 2) twice out of every three cycles, don't fire on third, between 7 AM and 10 PM use #4 exclusively)
b) Decided automatically by the pacing device based upon hemodynamic measurements, time of day, preset limits, activity sensors, myocardial measurements, or some other combination of parameters.

In some embodiments, a multiple lead/multiple electrode device may have the ability to stimulate the atrium ahead of the ventricle, giving the atrium a chance to push a bit more blood into the ventricle before the ventricle begins to contract. For example, there may be one or more electrodes in the right atrium and one or more in the right ventricle. The pacing unit may send a pulse causing the right atrium to contract while inhibiting the right ventricle from contracting. It may then later remove the inhibit signal from the right ventricle and stimulate it to cause the right ventricle to contract. Thus, the pacing device may cause a time delay between the contraction of the right atrium and the right ventricle.

Since the pacing system may have a pressure sensor in the right ventricle and/or right atrium, the pacing system may use that information to determine the delay between contraction of the right atrium and the right ventricle. For example, the right atrium may be paced to contract while the left ventricle is given a signal that inhibits contraction. The pacing device monitors the pressure in the right atrium and/or right ventricle until it increases to a certain threshold (probably some number of units of pressure above the lowest pressure observed in that cycle). Once the pressure signal crosses some threshold (or after a certain period of time, which ever is first), the pacing system would remove the inhibit signal(s) from the right ventricle and cause it to contract.

Similarly, this process may be extended to the left side of the heart. Thus, for certain hearts (but probably not all hearts) the patient may benefit by a system where both atriums contract before both ventricles. An electrode placed in the atrial septum, which causes both atria to contract simultaneously, in this case stimulates the left atrium. An electrode inserted into a coronary vein over the left ventricle, in this case, stimulates the left ventricle to contract.

Some patients may further benefit from a delay between the left ventricular and right ventricular contractions, using a similar inhibit strategy for both ventricles. Thus, the left and right atrium may fire first while the other two ventricles are inhibited, then the right ventricle may fire a short time later, when, for example the pressure in the right ventricle has reached some threshold, then, a short while later, the left ventricle fires, after it has reached its own threshold. This may be useful in cases where the left atrium is helping a stiff left ventricle (diastolic disease) fill with blood. In such cases, the left ventricle may need somewhat more time to accomplish this task, while the right ventricle may not be affected by this diastolic disease to the same extent, and therefore contracts somewhat earlier than the left ventricle. So there could be multiple delays between pacing various regions of the heart.

Similarly, muscles that control various valves may be selectively paced or inhibited before or after the rest of that chamber has its inhibition signal removed. Thus a "slow valve" may benefit from a pacing signal to cause it to start opening or closing a bit earlier than the contraction begins. This would effectively reduce the flow resistance of valves that are slow to open or, possibly, increase the flow resistance of valves that are slow to close. Both inhibition signals and contraction signals may be used to effect these changes. So, in addition to using multiple electrodes on multiple leads to sequentially pace the various chambers of the heart, portions of a chamber may be selectively paced or inhibited to enhance overall cardiac function.

Many electrophysiologists who implant pace makers work only on the right side of the heart. Therefore, it is advantageous to develop a method to optimize pacing results using only catheters inserted into the right side of the heart. In this case, a catheter with the ability to measure velocity and cross sectional area could be placed in the pulmonary artery to measure each stroke volume and thus a per-stroke measurement of cardiac output. In addition, right atrial pressure could be used with systolic blood pressure measured with a blood pressure cuff to estimate systemic vascular resistance. In addition, blood oxygenation in the right side of the heart may be measured using a catheter with either an optical sensing system or some other oxygen sensing system, such as withdrawing blood and measuring it optically or using an on-catheter blood-oxygenation measuring device. These parameters may be used to optimize the settings of the pace-maker. Thus, the pacing device may be. optimized by using values measured only from devices inserted into the right side of the heart or placed external to the patient.

The use of right ventricular blood oxygen concentration to determine heart rate has already been described. This method may work within a tight pacing range with no further information. In some patients, for example those with lung disease or those traveling to a high altitude, setting a heart rate solely on this parameter may cause an excessively high heart rate. Thus, it may be preferable to use both left and right blood oxygen concentrations. For these and other reasons, it may be desirable to use blood oxygen concentration(s) and systemic vascular resistance to control heart rate. In this case, it may be desirable to have an implanted sensor directly measuring cardiac output. For example, using a device placed on a pacing lead in the tricuspid valve, one may measure the diameter of the valve and the velocity profile of the blood flowing through it. Thus, if the blood oxygen concentration(s) signals an increase in heart rate but the systemic vascular resistance (calculated from the aforementioned cardiac output sensor and the pressure sensors on either side of the ventricular septum) does not signal an increase in activity, then the heart rate may be left unchanged, or kept within a relatively narrow range. If, on the other hand, the vascular resistance indicates an increase in exercise level and a drop in the blood oxygen concentration confirms that signal, then the heart rate may be increased within a broader limit range. Thus, it is possible to use the combination of blood oxygen concentration and systemic vascular resistance to control heart rate.

Some embodiment of the device may be used with patients with or expected to develop a shunt. A leak of oxygenated blood from the left to the rights side of the heart would tend to elevate the right sided blood oxygen concentration above that seen in the vena cava, and thus, if used to set heart rate, would lead to a lower than desirable heart rate. If a shunt exists, develops or is expected in a patient, the device may be implanted with an electronic cardiac output sensor multiplexed into the pacing lead or perhaps attached to a separate lead that floats in the pulmonary artery. Alternatively or additionally, a blood oxygen sensor may be placed on the lead in the superior vena cava as well as in the right ventricle. A divergence of signals from the vena cava and the left ventricle would indicate the presence of a shunt. Thus, the pacing device could use the blood oxygen levels in the superior and/or inferior vena cava instead of the blood oxygen level in the left ventricle to help determine heart rate. In addition, the cardiac output sensor may be used in conjunction with the left and right pressures available to a trans-septal implant to determine systemic vascular resistance. It is likely that measurements such as systemic vascular resistance do not need to be made every heart beat, but rather sampled at a less frequent pace unless they seem to be changing rapidly.

A diseased heart often fails faster on the left side than on the right. This asynchronous function may lead to a dysfumctional response to temporary volume overload, which may quickly cause the heart spiral into severe heart failure. Thus, some embodiments of the invention involve measuring both left and right ventricular pressures to set the delay between the Right Atrial and Right Ventricular contractions. By varying this delay, one may control the output of the right ventricle and thus control the left ventricular end diastolic pressure to a desired level.

Thus, in one embodiment a method of Atrial-Ventricular (A-V) pacing varies the efficiency of the right ventricle to actively control the end diastolic pressure of the left ventricle within a desired range. This "LVEDP Control Range" may be a function of other sensors, such as activity or blood oxygen or systemic vascular resistance sensors, so that higher operating pressures are available when there is a biological need for it, but lower when the patient is not exercising. The efficiency and thus the stroke volume of the right ventricle is varied by adjusting the timing delay between when the Atrium contracts and when the Ventricle contracts. Thus, if a sensor measures the LVEDP to be above the LVEDP Control Range, the pacing system will shorten the time delay between when the Right Atrium contracts and when the Right Ventricle contracts. In some cases, the doctor may allow the pacing system to let the ventricle contract before the atrium, further reducing its efficiency and stroke volume.

In addition, the pacing system may also measure right ventricular pressure. In this case, the timing of the delay between the Atrium contracting and the Ventricle contracting is determined by the pressure in the right ventricle. Thus, the right ventricle would be stimulated to contract when a certain pressure in the right ventricle has been reached. If the pacing system determines that the LVEDP needs to be reduced, it would set a lower pressure limit when the right ventricle would be stimulated. Thus, the right ventricle would contract before it is fully filled, and the right stroke volume would be reduced, reducing the LVEDP during the next cycle. Conversely, when it is desirable to increase the LVEDP, the limit pressure for the stimulation of the right ventricle would be increased, giving the atrium more time to fully contract and increase the preload of the right ventricle. Of course, other limits could be put in place, so that the once a maximum delay time has been reached or if the LVEDP starts to drop, the right ventricle is stimulated to contract.

In addition, the pacing system may start the pacing cycle at a lower end diastolic pressure. In this use, the atrium and/or ventricle would be paced based upon the pressure in the right ventricle. Once the pressure in the ventricle exceeded a certain pressure after first dropping below some other threshold, the contraction cycle would begin. Starting the contraction at a lower end diastolic right pressure would lead to a lower end-systolic right pressure, ultimately leading to a lower LVEDP. Since this approach may increase the heart rate by starting the cycle earlier than would otherwise occur, there would likely be upper limits placed on heart rate.

In some cases, below a normalized end diastolic pressure, the output of the left ventricle is matched to that of the right. In this case, Normalized End Diastolic Pressure is defined as the end diastolic pressure of a ventricle divided by the end diastolic pressure of that ventricle at the highest stroke volume where the stroke volumes of each side are matched. By definition, NEDP equals one when the stroke volume of the left ventricle begins to drop below the stroke volume of the right ventricle. In a healthy individual, NEDP will equal one at a fairly high stroke volume. During exercise, however, increases in LVEDP above the point where NEDP=1 leads to an accumulation of blood in the pulmonary vessels. So in this case, an increase in output by the right ventricle may lead to higher pulmonary pressures, which increases the pulmonary vascular resistance.

In yet another embodiment of the invention, two leads may be used, each lead having at least one pressure sensor. A first lead may be positioned within the right atrium and/or right ventricle, while a second lead may be positioned in the coronary vein via the coronary sinus. One or more pressures may be measured by the first and second leads, and the pressures measured by the second lead may be used to estimate/extrapolate a left ventricular pressure, such as left end diastolic pressure. These measured intracardiac pressures may then be compared to ambient pressure, which may be estimated using a pressure sensor implanted near the pacing can and under the skin, to determine adjustments to be made to the firing of the leads. For example, timing and/or timing delay of the leads may be adjusted based on the measured pressures. Alternatively, any other suitable adjustments may be made, and of course, any other parameters may be measured based by the leads, depending on the sensors they carry.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of enhancing cardiac pacing, the method comprising:

measuring at least one characteristic of a heart using one or more parameter measuring devices disposed in the heart, calculating at least one cardiac performance parameter using the at least one measured characteristic;

accepting at least one command from a user, said command assigning a relative weight to said at least one cardiac performance parameter, and automatically adjusting at least one functional parameter of a cardiac pacing device, wherein said adjusting comprises determining said adjustment to be made to the at least one functional parameter based on the at least one cardiac performance parameter and said assigned relative weight of said at least one cardiac performance parameter.

2. A method as in claim 1, wherein the at least one functional parameter is automatically adjusted based on the at least one calculated cardiac performance parameter.

3. A method as in claim 1, wherein measuring the at least one characteristic comprises measuring with at least one sensor device implanted in at least one wall of the heart.

4. A method as in claim 1, wherein measuring the at least one characteristic comprises measuring with at least one catheter device disposed in at least one chamber of the heart.

5. A method as in claim 4, wherein measuring the at least one characteristic further comprises measuring with at least one sensor device implanted in at least one wall of the heart.

6. A method as in claim 4, wherein the at least one catheter comprises a catheter positioned only in the right side of the heart.

7. A method as in claim 4, wherein the at least one catheter comprises a multiplexed catheter.

8. A method as in claim 7, wherein the at least one multiplexed catheter is disposed at least partially within at least one of a left ventricle and a right ventricle of the heart.

9. A method as in claim 1, wherein measuring the at least one characteristic comprises measuring at least one of pressure, volume, blood flow velocity, blood oxygen concentration, carbon dioxide concentration, wall stress, wall thickness, force, electric charge, electric current and electric conductivity.

10. A method as in claim 9, wherein each characteristic is measured in at least one of a chamber of the heart, a wall of the heart and a blood vessel adjacent the heart.

11. A method as in claim 9, wherein measuring comprises:

measuring at least one blood oxygen concentration in at least one chamber on the left side of the heart; and measuring at least one blood oxygen concentration in at least one chamber on the right side of the heart.

12. A method as in claim 11, further comprising:

measuring a systemic vascular resistance; and automatically adjusting the cardiac pacing device based on at least one of the measured blood oxygen concentrations and on the measured systemic vascular resistance.

13. A method as in claim 1, wherein measuring the at least one characteristic comprises measuring at least one blood oxygen concentration in a patient having a shunt.

14. A method as in claim 13, further comprising positioning at least a portion of a parameter measuring device in at least one of a pulmonary artery, a superior vena cava, an inferior vena cave and a right ventricle, wherein the portion of the parameter measuring device includes means for measuring blood oxygen content.

15. A method as in claim 14, wherein automatically adjusting comprises adjusting the cardiac pacing device based on at least one blood oxygen content measured by the parameter measuring device.

16. A method as in claim 1, wherein calculating the at least one cardiac performance parameter comprises calculating at least one of ejection fraction, cardiac output, cardiac index, stroke volume, stroke volume index, pressure reserve, volume reserve, cardiac reserve, cardiac reserve index, stroke reserve index, myocardial work, myocardial work index, myocardial reserve, myocardial reserve index, stroke work, stroke work index, stroke work reserve, stroke work reserve index, systolic ejection period, stroke power, stroke power reserve, stroke power reserve index, myocardial power, myocardial power index, myocardial power reserve, myocardial power reserve index, myocardial power requirement, $dP/dt$, $d^2P/dt$, ejection contractility, cardiac efficiency, cardiac amplification, valvular gradient, valvular gradient reserve, valvular area, valvular area reserve valvular regurgitation, valvular regurgitation reserve, a pattern of electrical emission by the heart, concentration of oxygen in the cardiac vein, and a ratio of carbon dioxide to oxygen.

17. A method as in claim 1, wherein the cardiac pacing device comprises one or more pacing leads.

18. A method as in claim 17, wherein at least one of the pacing leads comprises two or more electrodes disposed along its length.

19. A method as in claim 18, wherein the two or more electrodes are multiplexed with the at least one pacing lead.

20. A method as in claim 1, wherein adjusting the at least one functional parameter comprises adjusting at least one of a selected electrode of the cardiac pacing device to be activated, a pulse width of an activation of the cardiac pacing device, a pulse amplitude, a pulse duration, a number of pulses per one cycle of the heart, a pulse polarity, a pulse duty cycle, a timing of pulses relative to a cycle of the heart and a timing of pulses from multiple electrodes of the pacing device relative to one another.

21. A method as in claim 1, wherein said method further comprises:
assigning a first relative weight to a first calculated cardiac performance parameter;
assigning a second relative weight to a second calculated cardiac performance parameter; and
determining said at least one adjustment to be made to the at least one functional parameter, based on the first and second calculated cardiac performance parameters and the first and second relative weights.

22. A method as in claim 21, further comprising:
assigning a third relative weight to a third calculated cardiac performance parameter; and
determining the at least one adjustment, based on the first, second and third calculated cardiac performance parameters and the first, second and third relative weights.

23. A method as in claim 21, further comprising:
determining at least one apparatus performance parameter of the cardiac pacing device;
assigning a third relative weight to the apparatus performance parameter; and
determining the at least one adjustment, based on the first and second calculated cardiac performance parameters, the at least one apparatus performance parameter and the first, second and third relative weights.

24. A method as in claim 23, wherein determining the at least one apparatus performance parameter comprises determining at least one of an energy consumption rate, a maximum current and a maximum voltage of the cardiac pacing device.

25. A method as in claim 1 further comprising accepting an additional command from the user, the additional command assigning a relative weight to at least one apparatus performance parameter, wherein adjusting the at least one functional parameter comprises determining the adjustment based on the at least one cardiac performance parameter, the at least one apparatus performance parameter and the assigned relative weights of each.

26. A method as in claim 1, further comprising providing at least one calculated cardiac performance parameter to a user in the form of data.

27. A method as in claim 26, wherein the data is provided as one or more images on a display monitor.

28. A method as in claim 26, further comprising accepting at least one command from the user, the command designating one or more of the calculated cardiac performance parameters to be provided to the user.

29. A method as in claim 26, further comprising:
measuring the at least one characteristic of the heart after the adjustment step;
calculating the at least one cardiac performance parameter using the at least one re-measured characteristic; and
automatically adjusting at least one functional parameter of a cardiac pacing device.

30. A method as in claim 29, wherein the measuring, calculating and adjusting steps are performed multiple times, and wherein the calculated cardiac performance parameter is provided to the user in the form of data for each adjustment of the functional parameter of the pacing device.

31. A method as in claim 30, wherein the data is provided to the user in the form of a three-dimensional graph on a display monitor.

32. A method as in claim 1, wherein automatically adjusting comprises setting the cardiac pacing device to fire with a timing such that it does not fire during each heart cycle.

33. A method as in claim 32, wherein the timing is selected from the group consisting of firing once every two cycles, once every three cycles and once every four cycles.

34. A method as in claim 32, wherein setting the cardiac pacing device further comprises selecting at least one firing pattern from a group of possible firing patterns.

35. A method as in claim 1 wherein automatically adjusting comprises causing the cardiac pacing device to stimulate at least a first chamber of the heart before stimulating at least a second chamber of the heart.

36. A method as in claim 35, wherein the cardiac pacing device stimulates the right atrium before stimulating the right ventricle.

37. A method as in claim 35, wherein the cardiac pacing device stimulates both atria before stimulating both ventricles.

38. A method as in claim 35, wherein the cardiac pacing device stimulates the right ventricle before stimulating the left ventricle.

39. A method as in claim 35, wherein the cardiac pacing device stimulates the right ventricle before stimulating the right atrium.

40. A method as in claim 35, wherein the cardiac pacing device stimulates the left ventricle before stimulating the right ventricle or the right atrium.

41. A method as in claim 35, wherein automatically adjusting further comprises:

comparing at least one left ventricular end diastolic pressure measured by the parameter measuring device with a p re-defined left ventricular end diastolic pressure control range; and adjusting the cardiac pacing device based on the comparison.

42. A method as in claim 41, further comprising:
measuring at least one right ventricular pressure; and
adjusting the cardiac pacing device based on the comparison and on the measured right ventricular pressure.

43. A method as in claim 1, wherein automatically adjusting comprises causing the cardiac pacing device to stimulate at least a first valve of the heart before stimulating at least a second valve of the heart.

44. A method as in claim 1, wherein measuring comprises:
measuring at least a first pressure using a first lead positioned in at least one of the right atrium and the right ventricle of the heart; and
measuring at least a second pressure using a second lead positioned in the coronary vein over the left ventricle of the heart.

45. A method as in claim 44, further comprising measuring an ambient pressure.

46. A method as in claim 44, wherein calculating comprises estimating a left ventricular pressure from the second pressure.

47. A method as in claim 44, wherein adjusting comprises adjusting timing of firing of the first and second leads.

48. A method as in claim 47, wherein adjusting the firing timing comprises adjusting the timing to minimize left ventricular end diastolic pressure.

49. A method as in claim 47, wherein adjusting the firing timing comprises adjusting the timing to minimize left ventricular end diastolic pressure in response to at least one measured parameter measured by at least one sensor.

50. A method as in claim 47, wherein adjusting the firing timing comprises adjusting the timing to increase left ventricular end diastolic pressure to increase cardiac output.

51. A method as in claim 47, wherein adjusting the firing timing comprises adjusting the timing to increase cardiac output in response to at least one measured parameter measured by at least one sensor.

52. A method of enhancing cardiac pacing as in claim 1, the method comprising:
measuring at least a first pressure using a first sensor positioned in at least one of the right atrium and the right ventricle of a heart;
measuring at least a second pressure using a second sensor positioned in the coronary vein over the left ventricle of the heart;
measuring an ambient pressure for use in calculating a gauge pressure; and
adjusting the cardiac pacing based on the measured first and second gauge pressures.

53. A method of enhancing cardiac pacing as in claim 1, the method comprising:
measuring at least one left ventricular end diastolic pressure;
measuring a proxy for ambient pressure for use in calculating a gauge pressure; and
adjusting the cardiac pacing based on the gauge pressure.

54. A method of enhancing cardiac pacing, the method comprising:
measuring at least one characteristic of a heart using one or more parameter measuring devices disposed in the heat;

calculating at least one cardiac performance parameter using the at least one measured characteristic; and
automatically adjusting at least one functional parameter of a cardiac pacing device, wherein said adjusting comprises:
assigning a first relative weight to a first calculated cardiac performance parameter;
assigning a second relative weight to a second calculated cardiac performance parameter;
determining at least one apparatus performance parameter of the cardiac pacing device;
assigning a third relative weight to said apparatus performance parameter; and
determining at least one adjustment to be made to the at least one functional parameter, based on the first and second calculated cardiac performance parameters, the at least one apparatus performance parameter and the first, second and third relative weights.

55. A method as in claim 54, wherein measuring the at least one characteristic comprises measuring with at least one sensor device implanted in at least one wall of the heart.

56. A method as in claim 54, wherein measuring the at least one characteristic comprises measuring with at least one catheter device disposed in at least one chamber of the heart.

57. A method as in claim 56, wherein measuring the at least one characteristic further comprises measuring with at least one sensor device implanted in at least one wall of the heart.

58. A method as in claim 56, wherein the at least one catheter comprises a catheter positioned only in the right side of the heart.

59. A method as in claim 56, wherein the at least one catheter comprises a multiplexed catheter.

60. A method as in claim 59, wherein the at least one multiplexed catheter is disposed at least partially within at least one of a left ventricle and a right ventricle of the heart.

61. A method as in claim 54, wherein measuring the at least one characteristic comprises measuring at least one of pressure, volume, blood flow velocity, blood oxygen concentration, carbon dioxide concentration, wall stress, wall thickness, force, electric charge, electric current and electric conductivity.

62. A method as in claim 61, wherein each characteristic is measured in at least one of a chamber of the heart, a wall of the heart and a blood vessel adjacent the heart.

63. A method as in claim 61, wherein measuring comprises:
measuring at least one blood oxygen concentration in at least one chamber on the left side of the heart; and
measuring at least one blood oxygen concentration in at least one chamber on the right side of the heart.

64. A method as in claim 63, further comprising:
measuring a systemic vascular resistance; and
automatically adjusting the cardiac pacing device based on at least one of the measured blood oxygen concentrations and on the measured systemic vascular resistance.

65. A method as in claim 54, wherein measuring the at least one characteristic comprises measuring at least one blood oxygen concentration in a patient having a shunt.

66. A method as in claim 65, further comprising positioning at least a portion of a parameter measuring device in at least one of a pulmonary artery, a superior vena cava, an inferior vena cava and a right ventricle, wherein the portion of the parameter measuring device includes means for measuring blood oxygen content.

67. A method as in claim 66, wherein automatically adjusting comprises adjusting the cardiac pacing device based on at least one blood oxygen content measured by the parameter measuring device.

68. A method as in claim 54, wherein calculating the at least one cardiac performance parameter comprises calculating at least one of ejection fraction cardiac output, cardiac index, stroke volume, stroke volume index, pressure reserve, volume reserve, cardiac reserve, cardiac reserve index, stroke reserve index myocardial work, myocardial work index, myocardial reserve, myocardial reserve index, stroke work, stroke work index, stroke work reserve, stroke work reserve index, systolic ejection period, stroke power, stroke power reserve, stroke power reserve index, myocardial power, myocardial power index, myocardial power reserve, myocardial power reserve index, myocardial power requirement, dP/dt, $d^2P/dt$, ejection contractility, cardiac efficiency, cardiac amplification, valvular gradient, valvular gradient reserve, valvular area, valvular area reserve, valvular regurgitation, valvular regurgitation reserve, a pattern of electrical emission by the head, concentration of oxygen in the cardiac vein, and a ratio of carbon dioxide to oxygen.

69. A method as in claim 54, wherein the cardiac pacing device comprises one or more pacing leads.

70. A method as in claim 69, wherein at least one of the pacing leads comprises two or more electrodes disposed along its length.

71. A method as in claim 70, wherein the two or more electrodes are multiplexed with the at least one pacing lead.

72. A method as in claim 54, wherein adjusting the at least one functional parameter comprises adjusting at least one of a selected electrode of the cardiac pacing device to be activated, a pulse width of an activation of the cardiac pacing device, a pulse amplitude, a pulse duration, a number of pulses per one cycle of the heart, a pulse polarity, a pulse duty cycle, a timing of pulses relative to a cycle of the heart and a timing of pulses from multiple electrodes of the pacing device relative to one another.

73. A method as in claim 54, wherein said determining the at least one apparatus performance parameter comprises determining at least one of an energy consumption rate, a maximum current and a maximum voltage of the cardiac pacing apparatus.

74. A method as in claim 54, further comprising:
assigning a fourth relative weight to a third calculated cardiac performance parameter; and
determining the at least one adjustment, based on the first, second and third calculated cardiac performance parameters, the apparatus performance parameter, and the first, second, third and fourth relative weights.

75. A method as in claim 54, further comprising providing at least one calculated cardiac performance parameter to a user in the form of data.

76. A method as in claim 75, wherein the data is provided as one or more images on a display monitor.

77. A method as in claim 75, further comprising accepting at least one command from the user, the command designating one or more of the calculated cardiac performance parameters to be provided to the user.

78. A method as in claim 75, further comprising:
measuring the at least one characteristic of the heart after the adjustment step;
calculating the at least one cardiac performance parameter using the at least one re-measured characteristic; and
automatically adjusting at least one functional parameter of a cardiac pacing device.

79. A method as in claim 78, wherein the measuring, calculating and adjusting steps are performed multiple times, and wherein the calculated cardiac performance parameter is provided to the user in the form of data for each adjustment of the functional parameter of the pacing device.

80. A method as in claim 79, wherein the data is provided to the user in the form of a three-dimensional graph on a display monitor.

81. A method as in claim 54, wherein automatically adjusting comprises setting the cardiac pacing device to fire with a timing such that it does not fire during each heart cycle.

82. A method as in claim 81, wherein the timing is selected from the group consisting of firing once every two cycles, once every three cycles and once every four cycles.

83. A method as in claim 81, wherein setting the cardiac pacing device further comprises selecting at least one firing pattern from a group of possible firing patterns.

84. A method as in claim 54, wherein automatically adjusting comprises causing the cardiac pacing device to stimulate at least a first chamber of the heart before stimulating at least a second chamber of the heart.

85. A method as in claim 84, wherein the cardiac pacing device stimulates the right atrium before stimulating the right ventricle.

86. A method as in claim 84, wherein the cardiac pacing device stimulates both atria before stimulating both ventricles.

87. A method as in claim 84, wherein the cardiac pacing device stimulates the right ventricle before stimulating the left ventricle.

88. A method as in claim 84, wherein the cardiac pacing device stimulates the right ventricle before stimulating the right atrium.

89. A method as in claim 84, wherein the cardiac pacing device stimulates the left ventricle before stimulating the right ventricle or the right atrium.

90. A method as in claim 84, wherein automatically adjusting further comprises:
comparing at least one left ventricular end diastolic pressure measured by the parameter measuring device with a pre-defined left ventricular end diastolic pressure control range; and
adjusting the cardiac pacing device based on the comparison.

91. A method as in claim 90, further comprising:
measuring at least one right ventricular pressure; and
adjusting the cardiac pacing device based on the comparison and on the measured right ventricular pressure.

92. A method as in claim 54, wherein automatically adjusting comprises causing the cardiac pacing device to stimulate at Feast a first valve of the heart before stimulating at least a second valve of the heart.

93. A method as in claim 54, wherein measuring comprises:
measuring at least a first pressure using a first lead positioned in at least one of the right atrium and the right ventricle of the heart; and
measuring at least a second pressure using a second lead positioned in the coronary vein over the left ventricle of the heart.

94. A method as in claim 93, further comprising measuring an ambient pressure.

95. A method as in claim 93, wherein calculating comprises estimating a left ventricular pressure from the second pressure.

96. A method as in claim 93, wherein adjusting comprises adjusting timing of firing of the first and second leads.

97. A method as in claim 96, wherein adjusting the firing timing comprises adjusting the timing to minimize left ventricular end diastolic pressure.

98. A method as in claim 96, wherein adjusting the firing timing comprises adjusting the timing to minimize left ventricular end diastolic pressure in response to at least one measured parameter measured by at least one sensor.

99. A method as in claim 96, wherein adjusting the firing timing comprises adjusting the timing to increase left ventricular end diastolic pressure to increase cardiac output.

* * * * *

UNITED STATES PATENT AND TRADEMARK OFFICE
CERTIFICATE OF CORRECTION

| | |
|---|---|
| PATENT NO. | : 7,200,439 B2 |
| APPLICATION NO. | : 10/764429 |
| DATED | : April 3, 2007 |
| INVENTOR(S) | : Mark Zdeblick et al. |

It is certified that error appears in the above-identified patent and that said Letters Patent is hereby corrected as shown below:

In column 3 line 43 please delete the word "head" and replace with --heart--.

In column 25 line 5-6 please delete the word "Anziography" and replace with --Angiography--

In column 40 line 37-38 please delete the word "dysfumctional" and replace with --dysfunctional--.

Column 42, line 65
In claim 14: Please delete the word "cave" and replace with --cava--.

Column 45, line 67
In claim 54: Please delete the word "heat" and replace with --heart--.

Column 47, line 21
In claim 68: Please delete the word "head" and replace with --heart--.

Column 48, line 53
In claim 92: delete the word "Feast" and replace with --least--.

Signed and Sealed this

Fourteenth Day of August, 2007

JON W. DUDAS
*Director of the United States Patent and Trademark Office*